(12) United States Patent
Fujita et al.

(10) Patent No.: US 8,282,872 B2
(45) Date of Patent: Oct. 9, 2012

(54) (METH)ACRYLATE COMPOUND, CURABLE COMPOSITION USING THE SAME, CURABLE COMPOSITION FOR PHOTO-NANOIMPRINTS, CURED PRODUCT OF CURABLE COMPOSITION AND METHOD FOR MANUFACTURING CURED PRODUCT

(75) Inventors: Akinori Fujita, Fujinomiya (JP); Takashi Takayanagi, Fujinomiya (JP); Hiroyuki Yonezawa, Fujinomiya (JP)

(73) Assignee: FUJIFILM Corporation, Tokyo (JP)

( * ) Notice: Subject to any disclaimer, the term of this patent is extended or adjusted under 35 U.S.C. 154(b) by 218 days.

(21) Appl. No.: 12/921,081

(22) PCT Filed: Mar. 4, 2009

(86) PCT No.: PCT/JP2009/054041
§ 371 (c)(1),
(2), (4) Date: Sep. 3, 2010

(87) PCT Pub. No.: WO2009/110496
PCT Pub. Date: Sep. 11, 2009

(65) Prior Publication Data
US 2011/0003909 A1    Jan. 6, 2011

(30) Foreign Application Priority Data
Mar. 7, 2008  (JP) .................................. 2008-057703

(51) Int. Cl.
*C07C 69/90* (2006.01)
*C07C 69/94* (2006.01)
*C08F 2/48* (2006.01)
*C08F 20/26* (2006.01)
*C08F 20/40* (2006.01)
*H01L 21/027* (2006.01)

(52) U.S. Cl. ........ 264/446; 264/494; 522/182; 522/183; 560/100; 560/106; 560/183; 560/205

(58) Field of Classification Search ................... 522/182, 522/183; 560/100, 106, 183, 205; 264/446, 264/494
See application file for complete search history.

(56) References Cited

U.S. PATENT DOCUMENTS

| | | | |
|---|---|---|---|
| 3,784,578 A * | 1/1974 | Swodenk et al. ............. | 558/260 |
| 7,771,616 B2 * | 8/2010 | Irisawa et al. ............ | 252/299.62 |
| 8,163,813 B2 * | 4/2012 | Kawaguchi et al. .......... | 522/100 |
| 2004/0068026 A1 | 4/2004 | Kunita et al. | |
| 2010/0032621 A1 * | 2/2010 | Itano et al. ............... | 252/299.62 |
| 2010/0121013 A1 * | 5/2010 | Sakita et al. .................. | 526/323 |

FOREIGN PATENT DOCUMENTS

| | | |
|---|---|---|
| JP | 60-250020 A | 12/1985 |
| JP | 61-112161 A | 5/1986 |
| JP | 07-295221 A | 11/1995 |
| JP | 09-208525 A | 8/1997 |
| JP | 09-241182 A | 9/1997 |
| JP | 2004-115673 A | 4/2004 |
| JP | 2004-300315 A | 10/2004 |
| JP | 2007-073696 A | 3/2007 |
| JP | 2008-019292 A | 1/2008 |
| WO | WO2007/052403 * | 5/2007 |

OTHER PUBLICATIONS

International Preliminary Report on Patentability and Written Opinion of the International Searching Authority mailed Oct. 21, 2010 on International Application No. PCT/JP2009/054041.

* cited by examiner

*Primary Examiner* — Susan W Berman
(74) *Attorney, Agent, or Firm* — Sughrue Mion, PLLC

(57) ABSTRACT

It's object is to provide a (meth)acrylate compound excellent in photocurability, a curable composition comprising the compound and excellent in all of pattern accuracy, peelability, surface hardness, elasticity recovery and solvent resistance, an optical nanoimprint composition and a cured product of the curable composition and a method for producing it, especially to provide a composition favorable for a permanent film for flat panel displays, etc.

A (meth)acrylate compound represented by the following formula (1):

[Chemical 1]

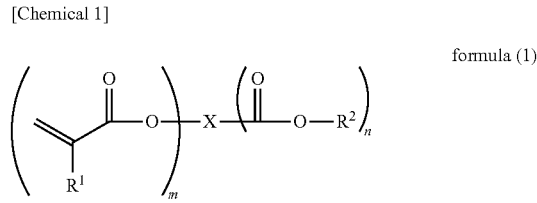

formula (1)

wherein $R^1$ represents a hydrogen atom or a methyl group, $R^2$ represents a substituent having carbon atoms of 2 to 6 and having a carbon-carbon double bond, X represents an organic group having carbon atoms of 1 to 10, m and n each are an integer of 1 to 3.

20 Claims, No Drawings

US 8,282,872 B2

(METH)ACRYLATE COMPOUND, CURABLE COMPOSITION USING THE SAME, CURABLE COMPOSITION FOR PHOTO-NANOIMPRINTS, CURED PRODUCT OF CURABLE COMPOSITION AND METHOD FOR MANUFACTURING CURED PRODUCT

TECHNICAL FILED

The invention relates to a novel (meth)acrylate compound and a curable composition using the same, a for photo nanoimprints, and a cured product thereof and a method therefore. Particularly, the invention relates to the invention relates to a curable composition for imprints suitable for manufacturing permanent films used for thin-film transistors for liquid crystal display, protective films for liquid crystal color filter, spacer and other materials for liquid crystal display, and cured products using the same and a method thereof.

BACKGROUND ART

Imprint technology is a development advanced from embossing technology well known in the art of optical disc production, which comprises pressing a mold original with an embossed pattern formed on its surface (this is generally referred to as "mold", "stamper" or "template") against a resin to thereby accurately transfer the micropattern onto the resin through mechanical deformation of the resin. In this, when a mold is once prepared, then microstructures such as nanostructures can be repeatedly molded, and therefore, this is economical, and in addition, harmful wastes and discharges from this nanotechnology are reduced. Accordingly these days, this is expected to be applicable to various technical fields.

Two methods of imprint technology have been proposed; one is a thermal imprint method using a thermoplastic resin as the material to be worked (for example, see S. Chou, et al., Appl. Phys. Lett. Vol. 67, 3114 (1995)), and the other is a photoimprint method using a photocurable composition (for example, see M. Colbun, et al., Proc. SPIE, Vol. 3676, 379 (1999)). In the thermal imprint method, a mold is pressed against a polymer resin heated up to a temperature not lower than the glass transition temperature thereof, then the resin is cooled and thereafter released from the mold to thereby transfer the microstructure of the mold onto the resin on a substrate. The method is applicable to various resin materials and glass materials and is expected to be applicable to various fields. For example, U.S. Pat. Nos. 5,772,905 and 5,956,216 disclose a imprint method of forming nanopatterns inexpensively.

On the other hand, in the photoimprint method where a composition for photoimprints is photocured by photoirradiation through a transparent mold or a transparent substrate, the transferring material does not require heating in pressing it against the mold, and therefore the method enables room-temperature imprinting. Recently, new developments having the advantages of the above two as combined, have been reported, including a nanocasting method and a reversal imprint method for forming three-dimensional structures.

For the imprint methods as above, proposed are applied technologies to nano-scale mentioned below.

In the first technology, the molded pattern itself has a function, and is applied to various elements in nanotechnology and to structural members. Its examples include various micro/nano optical elements and high-density recording media, as well as structural members in optical films, flat panel displays, etc. The second technology is for hybrid-molding of microstructures and nanostructures, or for construction of laminate structures through simple interlayer positioning, and this is applied to production of μ-TAS (micro-total analysis system) andbiochips. In the third technology, the formed pattern is used as a mask and is applied to a method of processing a substrate through etching or the like. In these technologies, high-precision positioning is combined with high-density integration; and in place of conventional lithography technology, these technologies are being applied to production of high-density semiconductor integrated circuits and transistors in liquid-crystal displays, and also to magnetic processing for next-generation hard discs referred to as patterned media. Recently, the action on industrialization of the above-mentioned imprint technologies and their applied technologies has become active for practical use thereof.

As an example of application of a nanoimprinting method, first described is a practical application thereof to formation of high-density semiconductor integrated circuits. Recently, semiconductor integrated circuits are being toward advanced micropatterning and increased density; and for realizing the intended micropatterning technology, high-accuracy photolithographic devices for pattern transfer are being much advanced. However, for satisfying the requirements for further more accurate micropatterning, the microprocessing method is being near to the wavelength of the light source in photoexposure, and the conventional lithographic technology is being near the end of its limit. Accordingly, in place of the lithographic technology for furthermore advanced micropatterning and further more increased accuracy, an electron-beam drawing system, a type of charged particle radiation system is being used in the art. The method of patterning with electron beams from such an electron-beam drawing system comprises a step of drawing via a mask pattern, different from the method for a one-shot exposure system of patterning with a light source such as an i-ray, an excimer laser or the like. Accordingly, when the number of the patterns to be drawn increases more, a longer time for photoexposure (drawing) is taken, and it is said that the defect with the method is that much time is taken for patterning. Therefore, with the drastic increase in the integration degree of semiconductor integrated circuits from 256 mega to 1 giga and to 4 giga, the patterning for them may take a drastically prolonged time, and the throughput may be thereby greatly lowered. Accordingly, for speeding up the patterning in the electron-beam drawing system, development of a one-shot irradiation exposure system, in which various shapes of masks are combined and are irradiated with electron beams all at a time to thereby form complicated electron beams, is being advanced. In this, the degree of micropatterning could be increased more, but the method is defective in that it requires a large-sized electron-beam drawing system and requires an additional mechanism of more accurately controlling the mask alignment, and therefore the apparatus cost for the method increases.

As opposed to this, as a technique of formation of micropatterns at a low cost, use of nanoimprint lithography technology (photonanoimprinting method) is under investigation. For example, Patent Document 1 and Patent Document 3 mentioned below disclose a nanoimprinting technology of forming a microstructure of at most 25 nanometers through pattern transfer using a silicon wafer as the stamper. Patent Document 4 mentioned below discloses a nanoimprinting composite composition applicable to the field of semiconductor microlithography.

Along the stream, investigations of production technology for micropatterning molds, mold durability, mold production cost, peelability of resin from mold, imprint uniformity, alignment accuracy and inspection technology for application of nanoimprinting lithography to the production of semiconductor integrated circuits are being much activated.

Next described is practical application of a photonanoimprinting method to flat displays such as liquid-crystal displays (LCD) and plasma displays (PDP).

With the recent tendency toward large-size and high-precision LCD substrates and PDP substrates, photonanoimprinting lithography as a type of inexpensive lithography has become specifically noted these days, in place of conventional photolithography for use in production of thin-film transistors (TFT) and electrode plates; and development of a photocurable resist in place of the etching photoresist for use in conventional photolithography has become necessary.

Also to the transparent protective film material for use for constructional elements in LCD and the like and to the spacer to define the cell gap in liquid-crystal displays, application of photonanoimprinting lithography is being investigated (for example, see Patent Documents 5 and 6). The resist for such constructional elements finally remains in the displays such as flat display panels, differing from the above-mentioned etching resist, and is therefore often referred to as "permanent resist" or "permanent film".

The permanent film to which conventional photolithography is applied includes, for example, a protective film to be provided on the TFT substrate of a liquid-crystal panel, and a protective film to be provided on a color filter for reducing the difference in level between R, G and B layers and for making the color filter resistant to high-temperature treatment in formation of an ITO film through sputtering thereon. Heretofore, as a transparent permanent film for color filter, used is a photocurable resin or a thermosetting resin such as siloxane polymer, silicone polyimide, epoxy resin, acrylic resin or the like (see Patent Documents 7 and 8 mentioned below). In forming such a protective film (permanent film), the film is required to have various characteristics such as uniformity of the coating film, adhesiveness thereof to substrate, high transmittance thereof after heat treatment at a temperature over 200° C., as well as smoothness, solvent resistance and scratching resistance thereof.

In the field of spacers for use in liquid-crystal displays, a photocurable composition comprising a resin, a photopolymerizing monomer and an initiator is generally widely used in conventional photolithography (for example, see Patent Document 9). In general, the spacer is formed by patterning, on a color filter substrate after formation of color filter or formation of protective film for color filter thereon, a photocurable composition to form a pattern thereon having a size of from 10 µm to 20 µm or so, followed by post-baking under heat for curing it. The spacer for use in liquid-crystal displays is required to have various properties of high mechanical characteristics, hardness, developability, patterning accuracy, adhesiveness and the like.

Accordingly, it is desired to develop a photocurable composition favorable for forming a permanent film (permanent resist) such as the above-mentioned transparent protective film and spacer according to a nanoimprinting method.

With the tendency toward large-size substrates, a photocurable composition is required to satisfy coating film uniformity, and is much required to satisfy various severe requirements such as coating film thickness uniformity between the center part and the peripheral part of the substrate, and the dimensional uniformity for high resolution, and the requirements of the film thickness and the shape for the composition are being severer.

Heretofore, in the field of production of liquid-crystal display devices using a small-size glass substrate, a method of dropping a resist onto the center of the substrate followed by spinning it has been employed for resist coating (for example, see Non-Patent Document 3). However, the method of dropping onto the center followed by spinning the substrate could hardly satisfy the requirements except the coating uniformity. Accordingly, as an alternative technology, a novel resist coating method with a discharge nozzle system has become proposed, as applicable to large-size substrates after the fourth generation substrates, especially after the fifth generation substrates. In the resist coating method with a discharge nozzle system, the discharge nozzle and the substrate are relatively moved and a photoresist composition is applied on the entire surface of the substrate to be coated therewith; and for this, for example, proposed is a method of using a discharge nozzle system having a discharge port with a plurality of nozzle orifices aligned in lines or having slit-like discharge ports, through which a photoresist composition is discharged like strips, or a method of applying a photoresist composition onto the entire surface of a substrate to be coated therewith followed by spinning the substrate to control the thickness of the coating film. Accordingly, for application to the field of production of liquid-crystal display devices, a nanoimprinting curable composition is also required to satisfy coating uniformity thereof on substrates.

For improving the coatability with a positive photoresist, a pigment dispersion photoresist for color filter formation and a protective film for photomagnetic discs or the like, there is known a technique of adding various surfactants or the like to them (for example, see Patent Documents 10 to 17); and there is disclosed a case of using a photocurable resin that contains a fluorosurfactant as a photonanoimprinting etching resist for formation of semiconductor integrated circuits (for example, see Patent Document 18). Heretofore, however, no one knows a method for improving the coatability of a substrate with a nanoimprinting curable composition not containing pigment, dye and organic solvent as indispensable ingredients for a permanent film.

Further, in the photonanoimprinting method, the flowability of the photocurable composition in the cavity of the surface recesses of the mold having a pattern formed thereon, must be increased. In addition, the adhesiveness between the resist and the substrate (base, support) must be enhanced while the peelability between the mold and the resist is kept good. However, it is difficult to make the photonanoimprinting curable composition satisfy all the requirements of good flowability in the cavity, good peelability from the mold and good adhesiveness to the substrate.

The photocurable composition to be applied to nanoimprinting may be divided broadly into two types, a type of radical polymerization and a type of ionic polymerization, depending on the difference in the reaction mechanism therebetween, further including hybrid types of these. Curable compositions of all types are applicable to nanoimprinting; but because of the broad latitude thereof in material selection, in general, a radical polymerization-type curable composition is much used (for example, see Non-Patent Document 4). As the radical polymerization-type curable composition, generally used is a composition that contains a monomer or an oligomer having a radical-polymerizing vinyl group or a (meth)acrylic group, and a photopolymerization initiator. When irradiated with light, the radical-polymerizing curable composition undergoes chain polymerization as the radical generated by the action of the photopolymerization initiator thereon attacks the vinyl group, and therefore it forms a polymer. In case where a bifunctional or more polyfunctional monomer or oligomer is used, the composition may form a crosslinked structure. Non-Patent Document 5 mentioned below discloses a composition that comprises a low-viscosity, UV-curable monomer and can attain room-temperature imprinting.

The necessary properties of materials for photonanoimprinting lithography may often vary depending on the use thereof, but the materials may have some common features in point of the necessary process characteristics thereof irrespective of their use. For example, the main requirements shown in Non-Patent Document 6 mentioned below are coatability, adhesiveness to substrate, low viscosity (<5 mPa·s), peelability, low degree of curing shrinkage, rapid curability. Especially in the application field where low-pressure imprintability and reduction in film retention are required, the materials are much required to have a low viscosity. On the other hand, when the necessary characteristics are grouped for individual applications, for example, light refractivity and light transmittance are mentioned for optical members. For etching resists, the requirements are etching resistance and reduction in residual film thickness. It is a key point in material designing how to control the necessary characteristics and how to take the balance of the characteristics. Accordingly, the necessary characteristics greatly vary at least between a process material and a permanent film, and therefore the materials must be developed in accordance with the process and the application thereof. As a material to be applied to photonanoimprinting lithography, Non-Patent Document 6 mentioned below discloses a photocurable material having a viscosity of about 60 mPa·s (25° C.). Similarly, Non-Patent Document 7 mentioned below discloses a photosensitive fluororesin comprising a monomethacrylate as the main ingredient thereof and having a viscosity of 14.4 mPa·s, in which the peelability of the resin is enhanced.

Regarding compositions for photonanoimprinting, there are descriptions relating to the viscosity thereof as above; however, up to now, there is known no report relating the guideline for the planning of materials suitable to individual applications.

Patent Documents 19 and 20 mentioned below disclose a case of using a photocurable resin that contains an isocyanate group-having polymer and embossing it for formation of relief hologram or diffraction grating. Patent Document 21 mentioned below discloses a photonanoimprinting curable composition that contains a polymer, a photopolymerization initiator and a viscosity regulator.

Further, Non-Patent Document 8 mentioned below discloses examples of applying a photocurable radical-polymerizing composition that comprises (1) a polyfunctional acrylic monomer (2) a polyfunctional acrylic monomer, or (3) a combination of a polyfunctional acrylic monomer and a photopolymerization initiator, or a photocationic polymerizing composition that contains a photocurable epoxy compound and a photo-acid generator to nanoimprinting lithography, and checking them for thermal stability and mold releasability.

Non-Patent Document 9 mentioned below discloses a photonanoimprinting curable composition containing (1) a functional acrylic monomer, or (2) a functional acrylic monomer, a silicon-containing monofunctional acrylic monomer and a photopolymerization initiator, as a device to enhance the releasability between a photocurable resin and a mold and to solve the problem of film shrinkage after curing and sensitivity depression owing to photopolymerization retardation in the presence of oxygen.

Non-Patent Document 10 mentioned below discloses that use of a mold prepared by applying a photonanoimprinting curable composition that contains a monofunctional acrylic monomer, a silicon-containing monofunctional monomer and a photopolymerization initiator onto a silicon substrate followed by surface-treating it reduces pattern defects after molding. Non-Patent Document 11 mentioned below discloses that coating a silicon substrate with a photonanoimprinting curable composition that contains a silicon monomer, a trifunctional acrylic monomer and a photopolymerization initiator followed by $SiO_2$ molding brings about a composition excellent in resolution and coating uniformity. Non-Patent Document 12 discloses a case of forming a pattern size of 50 nm with a cationic polymerizing composition that comprises a combination of a specific vinyl ether compound and a photo-acid generator. The composition is characterized by low viscosity and rapid curability, but they say that its problem is poor template peelability.

As shown in Non-Patent Documents 8 to 12, various photocurable resins applicable to photonanoimprinting lithography are disclosed, which comprise an acrylic monomer, an acrylic polymer and a vinyl ether compound differing in the functional group therein; however, any sufficient disclosure is given therein that relates to a guideline for preferred types, optimum monomers and monomer combinations for curable compositions, and for optimum viscosity of monomers or resists, solution properties of preferred resists, and planning of materials for improving resist coatability. Accordingly, nothing is known relating to a combination of preferred materials for widely applying curable compositions to photonanoimprinting lithography; and the actual condition is that a photonanoimprinting curable composition capable of exhibiting satisfactory performance in various applications is not as yet proposed up to now.

In Non-Patent Documents 11 and 12, some low-viscosity compositions are disclosed, but in case where they are patterned through photocuring followed by heat treatment, the transmittance of the final cured film is low (as colored) and the hardness thereof is low, and it could not be said that their practical performance as a permanent film could be sufficient.

Non-Patent Documents 13 and 14 propose an inorganic/organic hybrid material comprising a mixture of a photofunctional crosslinking substance-processed silica sol, (meth) acrylic monomer and a photopolymerization initiator, and report its application to photonanoimprinting lithography. Non-Patent Documents 13 and 14 report a case of 200-nm line pattern formation with an imprinting material and the patternability of the material up to a line width of 600 nm as a molding material. However, the material is still problematic in that its releasability from mold is insufficient and the hardness of the cured film is low, and therefore the material is not always satisfactory. Non-Patent Documents 13 and 14 disclose low-viscosity material compositions; however, the transmittance of the cured film formed by patterning the composition through photocuring followed by heat treatment is low (that is, the cured film is colored), and the hardness thereof is low.

Patent Document 22 discloses a patterning method using a fluorine-containing curable resin for bettering the releasability from mold, and discloses a hard coat composition containing a surface-treated colloidal silica, a specific (meth)acrylic monomer, a leveling agent and a photopolymerization initiator; and this reports application of the composition to optical discs that satisfy both film hardness and curing shrinkage resistance. However, the composition is still insufficient in point of the releasability from mold and the substrate coatability thereof, and its application to photonanoimprinting lithography is difficult. Further, in case where the composition is heat-treated after photocuring, the resulting pattern is colored, its transmittance is low and therefore the composition is unsuitable to a permanent film that requires light transmittance.

Patent Document 23 mentioned below discloses a nanoimprinting photocurable composition that comprises a cyclic structure-having (meth)acrylate monomer for making the composition etchable in dry. However, when the composition is photo-cured and then heat-treated, the transmittance of the resulting film is also low as the film is colored, and the composition is hardly used for a permanent film that requires light transmittance, and in addition, the hardness and the solvent resistance of the cured film is insufficient.

On the other hand, Patent Document 24 mentioned below discloses a curable composition containing an aromatic alkenyl ester, and discloses the effect of allyl ester benzoate for viscosity reduction.

Patent Document 25 discloses an curable composition for inkjet that comprises a monomer having a photopolymerization site and a thermal reaction site in one molecule.

Patent Document 26 discloses a curable composition with an acrylate monomer having a vinyl ether group in one molecule.

As in the above, there are a lot of essential technical themes with a permanent film, such including, for example, patterning accuracy, adhesiveness, transparency after heat treatment at higher than 200° C., high mechanical property (strength against external pressure), scratching resistance, surface smoothness, solvent resistance and outgassing reduction in heat treatment. In case where a photonanoimprinting curable composition is applied to a permanent film, its important requirements are (1) uniformity of coating film, (2) transparency after heat treatment and (3) scratching resistance, like conventional resists with an acrylic resin.

In addition, the subject theme peculiar to photonanoimprinting curable compositions is that, in addition to the above (1) to (3), (4) the flowability of the resist composition in the recesses of mold is secured and the composition must have a low viscosity in the absence of a solvent or in the presence of a small amount of a solvent, and (5) after photocured, the film is readily peeled from the mold with no stickiness to the mold, and these must be taken into consideration, and the technical difficulty in planning the composition is thereby further increased.

A composition heretofore known for inject application and for protective film for photomagnetic discs, and a photo-nanoimprinting curable composition used as an etching resist may have some material intersections with photonanoimprinting curable compositions for use for formation of permanent films, but they significantly differ in point of the necessary properties thereof such as high-temperature heat treatment applicability and mechanical strength. Accordingly, in case where a photocurable resin for protective film for photomagnetic discs or for etching resists is directly used as a resist for a permanent film, then the resin could not provide a practicable film in point of the transparency, the mechanical strength and the solvent resistance. As in the above, though various materials are disclosed for photo-nanoimprinting curable compositions, but at present, any satisfactory guideline for planning a curable composition suitable for formation of a permanent film is not as yet shown.

[Patent Document 1] U.S. Pat. No. 5,772,905
[Patent Document 2] U.S. Pat. No. 5,956,216
[Patent Document 3] U.S. Pat. No. 5,259,926
[Patent Document 4] JP-T-2005-527110
[Patent Document 5] JP-A-2005-197699
[Patent Document 6] JP-A-2005-301289
[Patent Document 7] JP-A-2000-39713
[Patent Document 8] JP-A-H6-43643
[Patent Document 9] JP-A-2004-240241
[Patent Document 10] JP-A-7-230165
[Patent Document 11] JP-A-2000-181055
[Patent Document 12] JP-A-2004-94241
[Patent Document 13] JP-A-H4-149280
[Patent Document 14] JP-A-H7-62043
[Patent Document 15] JP-A-2001-93192
[Patent Document 16] JP-A-2005-8759
[Patent Document 17] JP-A-2003-165930
[Patent Document 18] JP-A-2007-84625
[Patent Document 19] JP-A-2004-59820
[Patent Document 20] JP-A-2004-59822
[Patent Document 21] JP-A-2006-114882
[Patent Document 22] JP-A-2000-143924
[Patent Document 23] JP-A-2007-186570
[Patent Document 24] JP-A-H10-251473
[Patent Document 25] WO2004/099272
[Patent Document 26] JP-A-2005-255854
[Non Patent Document 1] S. Chou et al.: Appl. Phys. Lett. Vol. 67,3114(1995)
[Non Patent Document 2] M. Colbun et al: Proc. SPIE, Vol. 3676, 379 (1999)
[Non Patent Document 3] Electronic Journal 121-123 No. 8 (2002)
[Non Patent Document 4] F. Xu et al.: SPIE Microlithography Conference,5374, 232(2004)
[Non Patent Document 5] D. J. Resnick et al.: J. Vac. Sci. Technol. B, Vol. 21,No. 6, 2624(2003)
[Non Patent Document 6] The latest resist material hand book, P1, 103-104(200, Johokiki Publishing)
[Non Patent Document 7] CMC Publishing Co., Ltd: Development and Apply of Nanoimprints, P159 to 160 (2006)
[Non Patent Document 8] N. Sakai et al.: J. Photopolymer Sci. Technol. Vol. 18, No. 4, 531(2005)
[Non Patent Document 9] M. Stewart et al.: MRS Buletin, Vol. 30, No. 12, 947(2005)
[Non Patent Document 10] T. Beiley et al.: J. Vac. Sci. Technol. B18(6), 3572(2000)
[Non Patent Document 11] B. Vratzov et al.: J. Vac. Sci. Technol. B21(6), 2760(2003)
[Non Patent Document 12] E. K. Kim et al.: J. Vac. Sci. Technol, B22(1),131(2004)
[Non Patent Document 13] Proc. SPIE Int. Soc. Opt. Eng., Vol. 6151, No. Pt2, 61512F(2006)
[Non Patent Document 14] Science and Industry, Vol. 80, No. 7, 322(2006)

DISCLOSURE OF THE INVENTION

Problems to be Resolved by the Invention

The hardness and the mechanical strength of the pattern (cured film) formed of a nanoimprinting curable composition can be enhanced by using a polyfunctional monomer capable of imparting a high-crosslinking density. However, a polyfunctional monomer is a high-viscosity compound, and under the limitation to low viscosity, it is difficult to form a cured film having satisfactory physical properties. Further, since a polyfunctional monomer polymerizes at once in photoirradiation, another problem with it is the residue in a resin mold.

Accordingly, the present inventors have assiduously studied and, as a result, have noted that an aromatic alkenyl ester and an allyl group are poorly polymerizable in photoirradiation but react in baking (heating) to from a crosslinking point. Specifically, an aromatic alkenyl ester and an allyl group can control their crosslinking (polymerizing) reaction, and therefore they could reduce the residue in a resin mold.

In addition, an alkenyl ester group and an allyl group can lower the viscosity of the compound having the group than that of the compound having a (meth)acrylate group. Accordingly, it is difficult to plan a low-viscosity/high-functional (meth)acrylate; but using an alkenyl ester group or an allyl group makes it possible to plan a low-viscosity/high-functional compound. Further, since the compound with an alkenyl ester group or an allyl group has a low viscosity, its another advantage is that an aromatic ring (benzene ring, naphthalene ring) that may contribute toward increasing the strength of a cured film but causes viscosity increase can be used as the mother skeleton of the compound.

However, as described in the above, Patent Document 24 discloses a curable composition comprising an aromatic alkenyl ester, indicating that allyl ester benzoate and the like are effective for viscosity reduction. However, the composition could not increase the surface hardness of the cured film, and nothing is disclosed therein relating to a means for increasing the film surface hardness.

Further, as described in the above, Patent Document 25 discloses a curable composition for inkjet, which comprises a monomer having a photopolymerization site and a thermal reaction site in one molecule. However, the composition has a high viscosity, and therefore could not be applied to photo-nanoimprinting lithography directly as it is. In addition, though the strength of the cured film is high, the coloration of the cured film is serious, and using the film as a spacer protective film for liquid-crystal color filters is problematic in point of the transparency of the film. Nothing is disclosed relating to a method for solving the problem.

Further, as described in the above, Patent Document 26 discloses a curable composition with an acrylate monomer having a vinyl ether group in one molecule. The composition has a low viscosity and could be applied to photonanoimprinting lithography; however, the hardness of the cured film is low and nothing is disclosed relating to a method for improving it.

Accordingly, a resist composition practicable as a permanent film and applicable to a photonanoimprinting method is not as yet proposed up to now.

As in the above, the present inventors have assiduously studied and, as a result, have found that when a (meth)acrylate compound is used as a polymerizing compound and when a curable composition comprising the compound is used, then the above-mentioned problems of the pattern transfer accuracy, the hardness of cured film, and the transparency after curing under heat can be solved, and the problem of adhesion (residue) of the curable composition to a resin mold, if used, can also be solved.

The invention has been made for solving the above-mentioned problems, and its object is to provide a (meth)acrylate compound excellent in photocurability, a curable composition comprising the compound and excellent in all of pattern accuracy, peelability, surface hardness, elasticity recovery and solvent resistance, an optical nanoimprint composition and a cured product of the curable composition and a method for producing it, especially to provide a composition favorable for a permanent film for flat panel displays, etc.

Means for Solving the Problems

A compound having a (meth)acrylate group and an unsaturated double bond-having ester group, especially an allyl ester group in one molecule polymerizes at the acrylate group thereof in photopolymerization, and the unsaturated double bond site in the ester group therein can be reacted during heating. Accordingly, the inventors have found that, in case where a compound having at least two curable functional groups that differ from each other in the property is used in a curable composition for nanoimprints, then the compound brings about an effect that little residue remains in an inexpensive resin mold since the composition is semi-cured during photopolymerization, and when the composition is completely cured by subsequent heating, then it may form a cured film having a satisfactory mechanical strength. Further, using a benzene ring or naphthalene ring-having compound in the composition enhances the solvent resistance of the cured film. In addition, the inventors have further found that the vinyl ester group and the allyl ester group is effective for reducing the viscosity of the compound having the group, and the compound is more excellent in nanoimprinting aptitude. Based on these findings, the inventors have known that the above-mentioned problems can be solved by the following means.

(1) A (meth)acrylate compound represented by the following formula (1):

[Chemical 1]

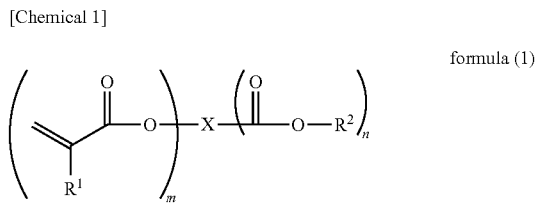

formula (1)

wherein $R^1$ represents a hydrogen atom or a methyl group, $R^2$ represents a substituent having carbon atoms of 2 to 6 and having a carbon-carbon double bond, X represents an organic group having carbon atoms of 1 to 10, m and n each are an integer of 1 to 3.

(2) The (meth)acrylate compound according to (1), wherein $R^2$ in the formula (1) is —$CH_2$—$CH$=$CH_2$.

(3) The (meth)acrylate compound according to (1), wherein $R^1$ in the formula (1) is a hydrogen atom.

(4) The (meth)acrylate compound according to any one of (1) to (3), wherein X in the formula (1) is a benzene ring or a naphthalene ring.

(5) The (meth)acrylate compound according to any one of (1) to (4), wherein m and n in the formula (1) each are 1 or 2.

(6) The (meth)acrylate compound according to (1) or (2), wherein $R^1$ in the formula (1) is a hydrogen atom, X in the formula (1) is a benzene ring or a naphthalene ring, and m and n in the formula (1) each are 1 or 2.

(7) The (meth)acrylate compound according to any one of (1) to (6), which has at least one partial structure selected from hydroxybenzoic acid, dihydroxybenzoic acid, dihydroxyphthalic acid and dihydroxynaphthoic acid.

(8) A curable composition comprising a photopolymerization initiator and the (meth)acrylate compound according to any one of (1) to (7).

(9) The curable composition according to (8), which further comprises a polymerizable monomer other than the (meth)acrylate compound represented by the formula (1).

(10) The curable composition according to (9), wherein the polymerizable monomer other than the (meth)acrylate compound represented by the formula (1) is a (meth)acrylate having a cyclic structure.

(11) The curable composition according to any one of (8) to (10), which further comprises a surfactant.

(12) The curable composition according to any one of (8) to (11), which further comprises an antioxidant.

(13) The curable composition according to any one of (8) to (12), which has a viscosity of 3 to 18 mPa·s at 25° C.

(14) The composition according to any one of (8) to (13), which is cured with photoirradiation.

(15) The composition according to any one of (8) to (14), which is cured by heating.

(16) A curable composition for nanoimprints, comprising a curable composition according to any one of (8) to (15).

(17) A cured product obtained by curing the curable composition according to any one of (8) to (16).

(18) A method for manufacturing a cured product, which comprises using the curable composition according to any one of (8) to (16).

(19) A method for manufacturing a cured product, which comprises applying the curable composition according to any one of (8) to (16) onto a substrate to form a patterning layer thereon, pressing a mold against a surface of the patterning layer, and irradiating the patterning layer with light.

(20) The method for manufacturing a cured product according to (19), which further comprises heating the patterning layer irradiated with light.

DETAILED DESCRIPTION OF THE INVENTION

The contents of the invention are described in detail hereinunder. In this specification, the numerical range expressed by the wording "a number to another number" means the range that falls between the former number indicating the lowermost limit of the range and the latter number indicating the uppermost limit thereof.

The contents of the invention are described in detail hereinunder. In this specification, "(meth)acrylate" means acrylate and methacrylate; "(meth)acrylic" means acrylic and methacrylic; "(meth)acryloyl" means acryloyl and methacryloyl. In the invention, monomer is differentiated from oligomer and polymer, and the monomer indicates a compound having a weight-average molecular weight of at most 1,000. In this specification, "functional group" means a group participating in polymerization.

"Nanoimprint" referred to in the invention means pattern transfer having a size of from several μm to several nm, and it is not limited to nano order.

Regarding the expression of "group (atomic group)" in this specification, the expression with no indication of "substituted" or "unsubstituted" includes both "substituted group" and "unsubstituted group". For example, "alkyl group" includes not only an alkyl group not having a substituent (unsubstituted alkyl group) but also an alkyl group having a substituent (substituted alkyl group).

[(Meth)acrylate Compound]

The curable composition of the invention comprises a photopolymerization initiator and at least one kind of a (meth)acrylate compound represented by the formula (1). Hereinafter, the (meth)acrylate compound represented by the formula (1) is described in detail.

In the formula (1), $R^1$ is a hydrogen atom or a methyl group. When $R^1$ is a methyl group, the methyl group may have a substituent. Examples of the substituent which $R^1$ may have include a halogen atom and an alkyloxy group. $R^1$ is preferably a hydrogen atom.

In the formula (1), $R^2$ is a substituent having carbon atoms of 2 to 6 and having a carbon-carbon double bond.

$R^2$ is preferably a linear or branched unsaturated hydrocarbon having carbon atoms of 2 to 6 or a cyclic unsaturated hydrocarbon having carbon atoms of 3 to 6. From the viewpoint of suppressing elevation of viscosity of the compound, $R^2$ is preferably an alkenyl group having carbon atoms of 2 to 3.

$R^2$ may have a substituent. The substituent which $R^2$ may have is not specifically limited. Examples of the substituent which $R^2$ may have include a halogen atom and an alkyloxy group.

$R^2$ may have two or more carbon-carbon double bonds and preferably has one carbon-carbon double bond.

The position of the carbon-carbon double bond in $R^2$ is not specifically limited. When the carbon-carbon double bond is between the carbon atoms other than the carbon atom at the edge of $R^2$, the carbon-carbon double bond may be cis or trans.

Specific examples of $R^2$ include a vinyl group, a propenyl group ($-CH=CH-CH_3$), an aryl group ($-CH_2-CH=CH_2$), a butynyl group, a pentenyl group, a 6-hexsenyl group, and a cyclohexenyl group. Of those, preferred are a vinyl group, a propenyl group ($-CH=CH-CH_3$), an aryl group ($-CH_2-CH=CH_2$), a butynyl group, a pentenyl group, a 6-hexsenyl group, and a cyclohexenyl group, and, more preferred is $-CH_2-CH=CH_2$.

X in the formula (1) is an organic group having carbon atoms of 1 to 10.

The organic group herein may include a group comprising at least one of a sulfur atom, a nitrogen atom and an oxygen atom as well as a hydrocarbon group. Those organic groups may be a cyclic group or a linear or branched group.

Examples of X include a linear or branched hydrocarbon group having carbon atoms of 1 to 10, a cyclic hydrocarbon group having carbon atoms 3 to 10, a hetero ring group having carbon atoms 3 to 10. Of those, preferred are an aromatic hydrocarbon group having carbon atoms 6 to 10 and a linear hydrocarbon group having carbon atoms of 3 to 6. Further preferred is an aromatic hydrocarbon group having carbon atoms 6 to 10 from the viewpoints of suppressing elevation of viscosity of the compound and compatibility to the other compounds.

Such an aromatic hydrocarbon group having carbon atoms 6 to 10 may be linked therein through an organic linking group as far as the carbon number is in 1 to 10 as a whole of X. The aromatic hydrocarbon group having carbon atoms 6 to 10 may have a monocyclic structure or a polycyclic structure. In the case of the polycyclic structure, it maybe a condensed polycyclic structure such as naphthalene. When X comprises a condensed polycyclic structure, X preferably comprises 2 or less of cyclic structures from the viewpoint of the viscosity.

X further may comprise a substituent. The substituent which X may comprise is not particularly limited. Examples thereof include a halogen atom and an alkyloxy group.

Specific examples of X include a benzene ring, a naphthalene ring and a pyridine ring, and X is preferably a benzene ring or a naphthalene ring.

n in the formula (1) is an integer of 1 to 3 and m is an integer of 1 to 3. Since the (meth)acrylate compound in the invention is a polyfunctional compound, the obtained cured membrane can attain strength.

The upper limits of n and m are not particularly limited, and n+m is preferably 4 or less, more preferably 3 or less from the viewpoints of viscosity and polymerization reactivity of the composition. The above n is preferably 1 or 2, more preferably 1. m is preferably 1 or 2, more preferably 2. Thus, n +m is preferably 2 to 6, more preferably 2 or 3 from the viewpoints of suppressing ascent of viscosity of the compound and attaining mechanical strength of the cured membrane.

Preferable examples of the compounds represented by the formula (1) in the invention are shown below, however, to which the invention is not limited.
[Chemical 2]
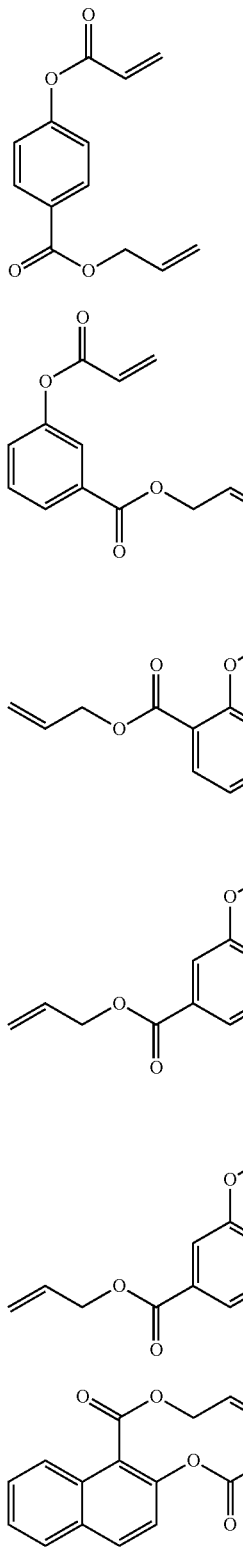
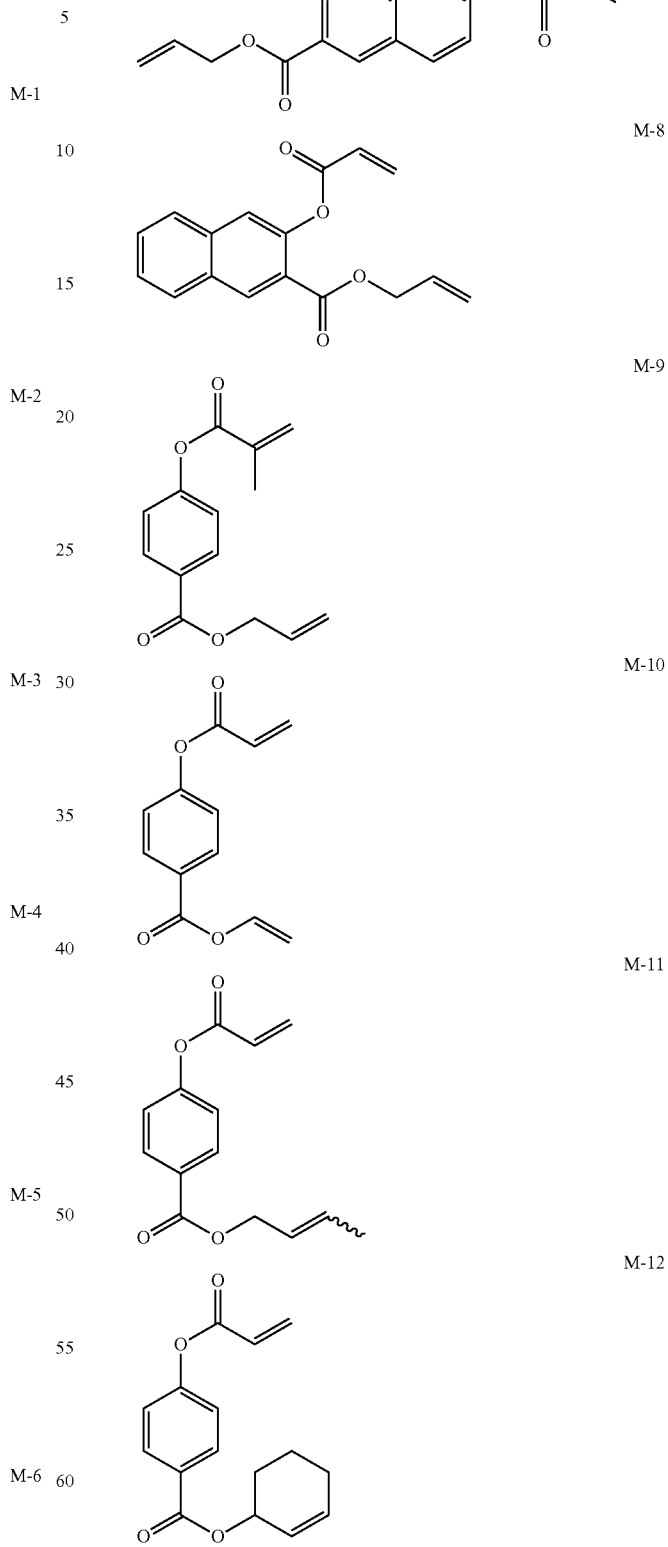
From the above mentioned viewpoints, the (meth)acrylate compound presented by the formula (1) is particularly preferably a (meth)acrylate compound comprising one partial structure selected from a (di)hydroxybenzonic acid, a hydroxyphthalic acid and a hydroxynapthoic acid.

[Curable Composition]

The curable composition of the invention preferably comprises a photopolymerization initiator and at least one kind of the (meth)acrylate compound represented by the formula (1).

—Content of the (Meth)acrylate—

The content of the compound represented by the formula (1) in the curable composition of the invention is preferably 5 to 90% by mass, more preferably 10 to 70% by mass, further more preferably 20 to 50% by mass from the viewpoints of adjustment of the viscosity of the composition, the peelability from the mold and attainment of the mechanical strength.

—Photopolymerization Initiator—

The curable composition of the invention comprises a photopolymerization initiator. The content of the photopolymerization initiator may be, for example, from 0.1 to 15% by mass of all the components constituting the curable composition, preferably from 0.2 to 12% by mass, more preferably from 0.3 to 10% by mass. In case where two or more different types of photopolymerization initiators are used, the total content thereof falls within the above range. When the content of the photopolymerization initiator is at least 0.1% by mass, then it is favorable since the sensitivity (rapid curability), the power of resolution, the line edge accuracy and the coating film strength of the curable composition tend to be better. On the other hand, when the content of the photopolymerization initiator is at most 15% by mass, it is also favorable since the light transmittance, the discoloration resistance and the handlability of the curable composition tend to be better. Heretofore, inkjet compositions and compositions for liquid-crystal display color filters containing dye and/or pigments have been variously investigated in point of the preferred amount of the photopolymerization initiator and/or the photoacid generator to be in the curable compositions; however, there is no report relating to the preferred amount of the photopolymerization initiator and/or the photoacid generator to be added to photocurable compositions for nanoimprints. In this connection, in the systems containing dye and/or pigment, the dye and/or the pigment may act as a radical-trapping agent and may have some influence on the photopolymerization and the sensitivity of the compositions. Taking this into consideration, the amount of the photopolymerization initiator to be added to these applications is optimized. On the other hand, in the curable composition of the invention, dye and/or pigment are not indispensable ingredients, and the optimum range of the photopolymerization initiator in the composition may differ from that in the field of inkjet compositions and compositions for liquid-crystal display color filters.

As the photopolymerization initiator used in the invention, a photopolymerization initiator active to the wavelength of the light source used and capable of generating a suitable active radical is used.

The photopolymerization initiator used in the invention is exemplified by a commercial-availavle photopolymerization initiator. Examples thereof include those disclosed in JP-A-H2008-105414, paragraph 0091.

The curable composition of the invention may comprise, as other ingredients, (A) another polymerizable monomer, (B) a surfactant and (c) an antioxidant in addition to the compound represented by the formula (1) and the photopolymerization initiator.

—(A) Other Polymerizable Monomer—

As mentioned above, the curable composition of the invention further may comprise a polymerizable monomer other than the above compound represented by the formula (1) for the purpose of improving the viscosity of the composition, the hardness of the cured film and the flexibility. The polymerizable monomer in the invention means a mono-functional or poly-functional polymerizable compound having a molecular weight of 1000 or less. The above other polymerizable monomer is exemplified by an ethylenic unsaturated bond-containing group, a compound having an oxirane ring (epoxy compounds), a vinyl ether compound, a styrene derivative, a compound comprising a fluorine atom, a propenyl ether and a butenyl ether, and is preferably a unsaturated polymerizable monomer having from 1 to 6 ethylenic unsaturated bond-containing groups from the viewpoint of acceleration of the curing at photoirradiation. More preferred is a unsaturated polymerizable monomer having one ethylenic unsaturated bond-containing group (mono-functional unsaturated polymerizable monomer).

The polymerizable unsaturated monomer having from 1 to 6 ethylenic unsaturated bond-having groups is described below.

The polymerizable unsaturated monomer having one ethylenic unsaturated bond-having group (mono-functional polymerizable unsaturated monomer) includes concretely 2-acryloyloxyethyl phthalate, 2-acryloyloxy-2-hydroxyethyl phthalate, 2-acryloyloxyethyl hexahydrophthalate, 2-acryloyloxypropyl phthalate, 2-ethyl-2-butylpropanediol acrylate, 2-ethylhexyl(meth)acrylate, 2-ethylhexylcarbitol(meth)acrylate, 2-hydroxybutyl(meth)acrylate, 2-hydroxyethyl(meth)acrylate, 2-hydroxypropyl(meth)acrylate, 2-methoxyethyl(meth)acrylate, 3-methoxybutyl(meth)acrylate, 4-hydroxybutyl(meth)acrylate, acrylic acid dimer, benzyl(meth)acrylate, butanediol mono(meth)acrylate, butoxyethyl(meth)acrylate, butyl(meth)acrylate, cetyl(meth)acrylate, ethyleneoxide-modified (hereinafter this may be referred to as "EO") cresol(meth)acrylate, dipropylene glycol (meth)acrylate, ethoxylated phenyl(meth)acrylate, ethyl (meth)acrylate, isoamyl(meth)acrylate, isobutyl(meth)acrylate, isooctyl(meth)acrylate, cyclohexyl(meth)acrylate, isobornyl(meth)acrylate, dicyclopentanyl(meth)acrylate, dicyclopentanyloxyethyl(meth)acrylate, isomyristyl(meth)acrylate, lauryl(meth)acrylate, methoxydiproylene glycol (meth)acrylate, methoxytripropylene glycol(meth)acrylate, methoxypolyethylene glycol(meth)acrylate, methoxytriethylene glycol(meth)acrylate, methyl(meth)acrylate, neopentyl glycol benzoate(meth)acrylate, nonylphenoxypolyethylene glycol(meth)acrylate, nonylphenoxypolypropylene glycol (meth)acrylate, octyl(meth)acrylate, paracumylphenoxyethylene glycol(meth)acrylate, epichlorohydrin (hereinafter referred to as "ECH")—modifiedphenoxyacrylate, phenoxyethyl(meth)acrylate, phenoxydiethylene glycol(meth)acrylate, phenoxyhexaethylene glycol(meth)acrylate, phenoxytetraethylene glycol(meth)acrylate, polyethylene glycol (meth)acrylate, polyethylene glycol-polypropylene glycol (meth)acrylate, polypropylene glycol(meth)acrylate, stearyl (meth)acrylate, EO-modified succinic acid(meth)acrylate, tert-butyl(meth)acrylate, tribromophenyl(meth)acrylate, EO-modified tribromophenyl(meth)acrylate, tridodecyl (meth)acrylate, p-isopropenylphenol, styrene, α-methylstyrene, acrylonitrile, vinylcarbazole, ethyl oxetanyl ethyl acrylate (OXE-10), (trimethoxysilyl) propyl acrylate (KBM5103), dicyclopentenyl acrylate, etc.

Of those, especially preferred for use in the invention are benzyl(meth)acrylate, 2-hydroxyethyl(meth)acrylate, trimethoxy propyl acrylate, and ethoxyethanol methyl acrylate, etc.

As the other polymerizable monomer, also preferred is a polyfunctional polymerizable unsaturated monomer having two or more ethylenic unsaturated bond-containing groups.

Preferred examples of the difunctional polymerizable unsaturated monomer having two ethylenic unsaturated bond-containing groups for use in the invention include diethylene glycol monoethyl ether(meth)acrylate, dimethylol-dicyclopentane di(meth)acrylate, di(meth)acrylated isocyanurate, 1,3-butylene glycol di(meth)acrylate, 1,4-butanediol di(meth)acrylate, EO-modified 1,6-hexanediol di(meth)acrylate, ECH-modified 1,6-hexanediol di(meth)acrylate, allyloxy-polyethylene glycol acrylate, 1,9-nonanediol di(meth)acrylate, EO-modified bisphenol A di(meth)acrylate, PO-modified bisphenol A di(meth)acrylate, modified bisphenol A di(meth)acrylate, EO-modified bisphenol F di(meth)acrylate, ECH-modified hexahydrophthalic acid diacrylate, hydroxypivalic acid neopentyl glycol di(meth)acrylate, neopentyl glycol di(meth)acrylate, EO-modified neopentyl glycol diacrylate, propyleneoxide (hereinafter referred to as "PO")-modified neopentyl glycol diacrylate, caprolactone-modified hydroxypivalate neopentyl glycol, stearic acid-modified pentaerythritol di(meth)acrylate, ECH-modified phthalic acid di(meth)acrylate, poly(ethylene glycol-tetramethylene glycol)di(meth)acrylate, poly(propylene glycol-tetramethylene glycol)di(meth)acrylate, polyester(di)acrylate, polyethylene glycol di(meth)acrylate, polypropylene glycol di(meth)acrylate, ECH-modified propylene glycol di(meth)acrylate, silicone di(meth)acrylate, triethylene glycol di(meth)acrylate, tetraethylene glycol di(meth)acrylate, dimethyloltricyclodecane di(meth)acrylate, neopentyl glycol-modified trimethylolpropane di(meth)acrylate, tripropylene glycol di(meth)acrylate, EO-modified tripropylene glycol di(meth)acrylate, triglycerol di(meth)acrylate, dipropylene glycol di(meth)acrylate, divinylethylene-urea, divinylpropylene-urea.

Of those, especially preferred for use in the invention are neopentyl glycol di(meth)acrylate, 1,9-nonanediol di(meth)acrylate, tripropylene glycol di(meth)acrylate, tetraethylene glycol di(meth)acrylate, hydroxypivalate neopentyl glycol di(meth)acrylate, polyethylene glycol di(meth)acrylate, etc.

Examples of the polyfunctional polymerizable unsaturated monomer having at least three ethylenic unsaturated bond-having groups include ECH-modified glycerol tri(meth)acrylate, EO-modified glycerol tri(meth)acrylate, PO-modified glycerol tri(meth)acrylate, pentaerythritol triacrylate, EO-modified phosphoric acid triacrylate, trimethylolpropane tri(meth)acrylate, caprolactone-modified trimethylolpropane tri(meth)acrylate, EO-modified trimethylolpropane tri(meth)acrylate, PO-modified trimethylolpropane tri(meth)acrylate, tris(acryloxyethyl)isocyanurate, dipentaerythritol hexa(meth)acrylate, caprolactone-modified dipentaerythritol hexa(meth)acrylate, dipentaerythritol hydroxy-penta(meth)acrylate, alkyl-modified dipentaerythritol penta(meth)acrylate, dipentaerythritol poly(meth)acrylate, alkyl-modified dipentaerythritol tri(meth)acrylate, ditrimethylolpropane tetra(meth)acrylate, pentaerythritol ethoxy-tetra(meth)acrylate, pentaerythritol tetra(meth)acrylate, etc.

Of those, especially preferred for use in the invention are EO-modified glycerol tri(meth)acrylate, PO-modified glycerol tri(meth)acrylate, trimethylolpropane tri(meth)acrylate, EO-modified trimethylolpropane tri(meth)acrylate, PO-modified trimethylolpropane tri(meth)acrylate, dipentaerythritol hexa(meth)acrylate, pentaerythritol ethoxy-tetra(meth)acrylate, pentaerythritol tetra(meth)acrylate, etc.

The oxirane ring-having compound (epoxy compound) includes, for example, polyglycidyl esters of polybasic acids, polyglycidyl ethers of polyalcohols, polyglycidyl ethers of polyoxyalkylene glycols, polyglycidyl ethers of aromatic polyols, hydrogenated polyglycidyl ethers of aromatic polyols, urethane-polyepoxy compounds, epoxidated polybutadienes, etc. One or more of these compounds may be used either singly or as combined.

Examples of the oxirane ring-having compound (epoxy compound) preferred for use in the invention include bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, hydrogenated bisphenol A diglycidyl ether, hydrogenated bisphenol F diglycidyl ether, hydrogenated bisphenol S diglycidyl ether, 1,4-butanediol diglycidyl ether, 1,6-hexanediol diglycidyl ether, glycerin triglycidyl ether, trimethylolpropane triglycidyl ether, polyethylene glycol diglycidyl ether, polypropylene glycol diglycidyl ether; polyglycidyl ethers of polyether polyols produced by adding one or more alkylene oxides to aliphatic polyalcohol such as ethylene glycol, propylene glycol, glycerin or the like; diglycidyl esters of aliphatic long-chain dibasic acids; monoglycidyl ethers of aliphatic higher alcohols; monoglycidyl ethers of polyether alcohols produced by adding alkyleneoxide to phenol, cresol, butylphenol or the like; glycidyl esters of higher fatty acids, etc.

Of those, especially preferred are bisphenol A diglycidyl ether, bisphenol F diglycidyl ether, hydrogenated bisphenol A diglycidyl ether, hydrogenated bisphenol F diglycidyl ether, 1,4-butanediol diglycidyl ether, 1,6-hexanediol diglycidyl ether, glycerin triglycidyl ether, trimethylolpropane triglycidyl ether, neopentyl glycol diglycidyl ether, polyethylene glycol diglycidyl ether, polypropylene glycol diglycidyl ether.

Commercial products favorable for use herein as the glycidyl group-having compound are UVR-6216 (by Union Carbide), Glycidol, AOEX24, Cyclomer A200 (all by Daicel Chemical Industry), Epikote 828, Epikote 812, Epikote 1031, Epikote 872, Epikote CT508 (all by Yuka Shell), KRM-2400, KRM-2410, KRM-2408, KRM-2490, KRM-2720, KRM-2750 (all by Asahi Denka Kogyo), etc. One or more of these may be used either singly or as combined.

The production method for the oxirane ring-having compounds is not specifically defined. For example, the compounds may be produced with reference to publications of Lecture of Experimental Chemistry 20, 4th Ed., Organic Synthesis II, p. 213, ff. (Maruzen, 1992); The chemistry of heterocyclic compounds—Small Ring Heterocycles, Part 3, Oxiranes (edited by Alfred Hasfner, John & Wiley and Sons, An Interscience Publication, New York, 1985); Yoshimura, Adhesive, Vol. 29, No. 12, 32, 1985; Yoshimura, Adhesive, Vol. 30, No. 5, 42, 1986; Yoshimura, Adhesive, Vol. 30, No. 7, 42, 1986; JP-A-11-100378, Japanese Patents 2906245 and 2926262.

As the other polymerizable monomer for use in the invention, vinyl ether compounds may be in the composition.

Any known vinyl ether compounds are usable, including, for example, 2-ethylhexyl vinyl ether, butanediol 1,4-divinyl ether, diethylene glycol monovinyl ether, ethylene glycol divinyl ether, triethylene glycol divinyl ether, 1,2-propanediol divinyl ether, 1,3-propanediol divinyl ether, 1,3-butanediol divinyl ether, 1,4-butanediol divinyl ether, tetramethylene glycol divinyl ether, neopentyl glycol divinyl ether, trimethylolpropane trivinyl ether, trimethylolethane trivinyl ether, hexanediol divinyl ether, tetraethylene glycol divinyl ether, pentaerythritol divinyl ether, pentaerythritol trivinyl ether, pentaerythritol tetravinyl ether, sorbitol tetravinyl ether, sorbitol pentavinyl ether, ethylene glycol diethylene vinyl ether, triethylene glycol diethylene vinyl ether, ethylene glycol dipropylene vinyl ether, triethylene glycol diethylene vinyl ether, trimethylolpropane triethylene vinyl ether, trimethylolpropane diethylene vinyl ether, pentaerythritol diethylene vinyl ether, pentaerythritol triethylene vinyl ether, pentaerythritol tetraethylene vinyl ether, 1,1,1-tris[4-(2-vinyloxyethoxy)phenyl]ethane, bisphenol A divinyloxyethyl ether, etc.

Of those, especially preferred for use in the invention are trimethylolpropane triethylene vinyl ether and bisphenol A divinyloxyethyl ether.

These vinyl ether compounds can be produced, for example, according to the method described in Stephen. C. Lapin, Polymers Paint Colour Journal, 179 (4237), 321 (1988), concretely through reaction of a polyalcohol or a polyphenol with acetylene, or through reaction of a polyalcohol or a polyphenol with a halogenoalkyl vinyl ether. One or more of these compounds may be used either singly or as combined.

As the other polymerizable monomer for use in the invention, styrene derivatives may also be employed. The styrene derivatives include, for example, styrene, p-methylstyrene, p-methoxystyrene, β-methylstyrene, p-methyl-β-methylstyrene, α-methylstyrene, p-methoxy-β-methylstyrene, p-hydroxystyrene, etc.

Examples of styrene derivatives which may be used as combined with the compound represented by the formula (1) include styrene, p-methylstyrene, p-methoxystyrene, β-methylstyrene, p-methyl-β-methylstyrene, α-methylstyrene, p-methoxy-β-methylstyrene, p-hydroxystyrene, divinyl styrene, etc.

Of those, especially preferred for use in the invention are divinyl styrene and p-methoxystyrene.

For the purpose of enhancing the releasability from mold and the coatability of the composition, a fluorine atom-having compound maybe incorporated into the composition. The compound includes, for example, trifluoromethyl(meth)acrylate, pentafluoroethyl(meth)acrylate, (perfluorobutyl)ethyl(meth)acrylate, perfluorobutyl-hydroxypropyl(meth)acrylate, (perfluorohexyl)ethyl(meth)acrylate, octafluoropentyl(meth)acrylate, perfluorooctylethyl(meth)acrylate, tetrafluoropropyl(meth)acrylate, etc.

As the other polymerizable monomer for use in the invention, propenyl ethers and butenyl ethers may also be employed.

Preferred examples of the propenyl ethers and butenyl ethers include, for example, 1-dodecyl-1-propenyl ether, 1-dodecyl-1-butenyl ether, 1-butenoxymethyl-2-norbornene, 1,4-di(1-butenoxy)butane, 1,10-di(1-butenoxy)decane, 1,4-di(1-butenoxymethyl)cyclohexane, diethylene glycol di(1-butenyl) ether, 1,2,3-tri(1-butenoxy)propane, propenyl ether propylene carbonate, etc.

The other polymerizable monomer as described above may be used singly or as combined.

The content for the other polymerizable monomer as described above varies depending on the content for the polymerizable compound of the invention in the composition, and is preferably a range from 10 to 99% by mass, more preferably a range from 20 to 80% by mass.

Next, the preferred blend embodiments of the (meth)acrylate compound and the other polymerizable compound (hereinafter, those compounds maybe referred to as "(total)polymerizable unsaturated monomer" as combined) are described below. The curable composition of the invention preferably comprises the (meth)acrylate represented by the formula (1) as the essential ingredient and preferably comprises the other polymerizable compound. The curable composition of the invention preferably comprises a (meth)acrylate compound comprising a ring structure as the other polymerizable monomer.

The preferable content of the other polymerizable monomer in the curable composition is explained.

A monofunctional polymerizable monomer is generally used as a reactive diluent, and has an effect of lowering the viscosity of the curable composition of the invention, and it is preferably added in an amount of from 5 to 90% by mass, more preferably from 10 to 80% by mass, even more preferably from 15 to 70% by mass, and particularly preferably from 15 to 50% by mass, relative to the amount of the (total) polymerizable unsaturated monomer.

A monomer having two polymerizable reactive groups (difunctional polymerizable monomer) is preferably added in an amount of from 10 to 90% by mass, more preferably from 20 to 80% by mass, and particularly preferably from 25 to 70% by mass, of all the polymerizable monomers.

The proportion of the monofunctional and difunctional polymerizable monomers to be added is preferably from 1 to 95% by mass, more preferably from 3 to 95% by mass, and particularly preferably from 5 to 90% by mass, of the (total) polymerizable unsaturated monomer.

The proportion of the polyfunctional polymerizable monomer having three or more unsaturated bond-having groups to be added is preferably from 5 to 80% by mass, more preferably from 10 to 70% by mass, and particularly preferably at most from 20 to 60% by mass, of all the polymerizable monomers. When the proportion of the polymerizable monomer having three or more polymerizable reactive groups is at most 80% by mass, it is favorable since the viscosity of the composition may be lowered.

—(B) Surfactant—

The curable composition of the invention may contain a surfactant. The content of the surfactant that may be in the composition may be, for example, from 0.001 to 5% by mass of the composition, preferably from 0.002 to 4% by mass, more preferably from 0.005 to 3% by mass. In case where two or more different types of surfactants are in the composition, the total amount thereof falls within the above range. When the surfactant content in the composition falls from 0.001 to 5% by mass, it is favorable from the viewpoint of the coating uniformity, therefore hardly worsening the mold transferability owing to excessive surfactant.

Preferably, the composition comprises at least one of a fluorine-containing surfactant, a silicone-type surfactant and a fluorine-containing silicone-type surfactant as the surfactant. More preferably, the composition comprises both of a fluorine-containing surfactant, a silicone-type surfactant, or a fluorine-containing silicone-type surfactant as the surfactant. Further more preferably, the composition comprises a fluorine-containing silicone-type surfactant as the surfactant.

"Fluorine-containing silicone-type surfactant" as referred to herein means a surfactant satisfying both the requirement of a fluorine-containing surfactant and that of a silicone-type surfactant.

Using the surfactant of the type may solve the problem of coating failures such as striation and flaky pattern formation (drying unevenness of resist film) that may occur when the curable composition of the invention is applied onto substrates on which various films are formed, for example, onto silicon wafers in semiconductor production, or onto glass square substrates, chromium films, molybdenum films, molybdenum alloy films, tantalum films, tantalum alloy films, silicon nitride films, amorphous silicon films, tin oxide-doped indium oxide (ITO) films or tin oxide films in production of liquid-crystal devices. In addition, the surfactant is effective for enhancing the flowability of the curable composition of the invention in the cavity of a female mold, for enhancing the mold-resist releasability, for enhancing the resist adhesiveness to substrates, and for lowering the viscosity of the composition. In particular, when the above-mentioned surfactant is added to the curable composition of the invention, the coating uniformity of the composition can be greatly improved; and in coating with it using a spin coater or a slit scan coater, the composition ensures good coating aptitude irrespective of the size of the substrate to which it is applied.

Examples of the nonionic fluorine-containing surfactant usable in the invention include Fluorad FC-430, FC-431 (Sumitomo 3M's trade names); Surflon S-382 (Asahi Glass's trade name); Eftop EF-122A, 122B, 122C EF-121, EF-126, EF-127, MF-100 (Tochem Products' trade names); PF-636, PF-6320, PF-656, PF-6520 (Omnova Solution's trade names); Futagent FT250, FT251, DFX18 (Neos' trade names); Unidyne DS-401, DS-403, DS-451 (Daikin's trade names); Megafac 171, 172, 173, 178K, 178A, F780F (Dai-Nippon Ink's trade names).

Examples of the nonionic silicone-type surfactant include SI-10 series (Takemoto Yushi's trade name), Megafac Paintad 31 (Dai-Nippon Ink's trade name), KP-341 (Shin-Etsu Chemical's trade name).

Examples of the fluorine-containing silicone-type surfactant include X-70-090, X-70-091, X-70-092, X-70-093 (Shin-Etsu Chemical's trade names); Megafac R-08, XRB-4 (Dai-Nippon Ink's trade names).

—(C) Antioxidant—

Preferably, the curable composition of the invention comprises a known antioxidant. The content of the antioxidant to be in the composition is, for example, from 0.01 to 10% by mass, preferably from 0.2 to 5% by mass. When two or more different types of antioxidants are in the composition, the total amount thereof falls within the above range.

The antioxidant is for preventing fading by heat or photoirradiation, and for preventing fading by various gases such as ozone, active hydrogen NOx, SOx (x is an integer), etc. Especially in the invention, the antioxidant added to the composition brings about the advantage that the cured film is prevented from being discolored and the film thickness is prevented from being reduced through decomposition. The antioxidant includes hydrazides, hindered amine-type antioxidants, nitrogen-containing heterocyclic mercapto compounds, thioether-type antioxidants, hindered phenol-type antioxidants, ascorbic acids, zinc sulfate, thiocyanates, thiourea derivatives, saccharides, nitrites, sulfites, thiosulfates, hydroxylamine derivatives, etc. Of those, preferred are hindered phenol-type antioxidants and thioether-type antioxidants from the viewpoint of their effect of preventing cured film discoloration and preventing film thickness reduction.

Commercial products of the antioxidant usable herein include Irganox 1010, 1035, 1076, 1222 (all by Ciba-Geigy); Antigene P, 3C, FR, Sumilizer S, Sumilizer GA80 (by Sumitomo Chemical); Adekastab AO70, AO80, AO503 (by Adeka), etc. These may be used either singly or as combined.

—Other Ingredient—

In addition to the above-mentioned ingredients, the curable composition of the invention may contain, if desired, photosensitizer, polymer ingredient, release agent, organic metal coupling agent, polymerization inhibitor, UV absorbent, light stabilizer, antiaging agent, plasticizer, adhesion promoter, thermal polymerization initiator, photobase generator, colorant, elastomer particles, photoacid enhancer, basic compound, flowability promoter, defoaming agent, dispersant, etc.

Further, in addition to the radical photopolymerization initiator, a photosensitizer may also be added to the curable composition of the invention for regulating the UV-region wavelength. Typical sensitizers usable in the invention are those disclosed in J. V. Crivello, Adv. in Polymer Sci., 62, 1 (1984), concretely including pyrene, perylene, acridine orange, thioxanthone, 2-chlorothioxanthone, benzoflavin, N-vinylcarbazole, 9,10-dibutoxyanthracene, anthraquinone, coumarin, ketocoumarin, phenanthrene, camphorquinone, phenothiazine derivatives, etc.

The curable composition of the invention may comprise a polyfunctional oligomer having a larger molecular weight than that of the above-mentioned, other polyfunctional monomer within a range capable of attaining the object of the invention, for the purpose of further increasing the crosslinking density of the composition. Examples of the photoradical-polymerizable polyfunctional oligomer include various acrylate oligomers such as polyester acrylates, urethane acrylates, polyether acrylates, epoxy acrylates.

The curable composition for nanoimprints of the invention may comprise any other polymer ingredient for the purpose of enhancing the dry etching resistance, the imprint aptitude and the curability of the curable composition. The polymer ingredient is preferably a polymer having a polymerizable functional group in the side chain thereof. The weight-average molecular weight of the polymer ingredient is preferably from 5000 to 500000, more preferably from 10000 to 30000, from the viewpoint of the miscibility of the polymer with the polymerizable monomers constituting the composition. The amount of the polymer ingredient to be added may be preferably from 0 to 30% by mass of the curable composition except the solvent therein, more preferably from 0 to 20% by mass, even more preferably from 0 to 10% by mass, most preferably at most 2% by mass. When the content of the polymer ingredient having a molecular weight of at least 2000 in the composition of the invention is at most 30% by mass of the composition except the solvent therein, then the patternability of the composition is bettered. From the viewpoint of the patternability of the composition, the resin content therein is preferably as small as possible, and except for the surfactant and other minor additives, preferably, the composition does not comprise any additional resin ingredient.

For the purpose of further enhancing the peelability, the curable composition of the invention may comprise a release agent. Specifically, the release agent is added for the purpose of neatly releasing a mold that was pressed into a layer of the composition of the invention, without causing the roughness of surface and without leaving a residual part of the curable composition of the invention adhered on the mold. The release agent usable in the invention may be known release agents including a silicone-type release agent, a solid wax such as a polyethylene wax, an amide wax, and Teflon® powder, a fluorine-type compound, and a phosphate-type compound. Those release agents may be adhered into a mold.

The silicone-type release agent is particularly excellent in peelability from the mold when combined with the composition of the invention, thereby hardly leaving a residual part of the composition of the invention adhered on the mold. The silocone-type release agent has an organopolysiloxane structure as the base structure. Examples thereof include a unmodified or modified silicone oil, a polysiloxane having trimethyl siloxysilicate, a silocone-type acryl resin. In addition, a silicone-type leveling agent which is generally used in a hard coating composition may be applied.

The modified silicone oil is that a polysiloxane is modified at a side chain and/or a terminal thereof, and is divided into a reactive silicone oil and an unreactive silicone oil. Examples of the reactive silicone oil include an amino-modified-type silicone oil, an epoxy-modified-type silicone oil, a carboxyl-modified-type silicone oil, a carbinol-modified-type silicone oil, a methacryl-modified-type silicone oil, a phenol-modified-type silicone oil, a reactive at one side terminal-type silicone oil, and a modified with different kinds of functional groups-type silicone oil. Examples of the unreactive silicone oil include a polyether-modified-type silicone oil, a methylstyryl-modified-type silicone oil, an alkyl-modified-type silicone oil, a higher fatty ester-modified-type silicone oil, a hydrophilia-specially modified-type silicone oil, a higher alkoxy-modified-type silicone oil, a higher fatty acid-modified-type silicone oil, and a fluorine-modified-type silicone oil.

Two or more modified methods are carried out to one poly siloxane molecular.

The modified silicone oil may have a moderate compatibility with ingredients of the composition. In particular, when a reactive oil having a reactivity with other ingredients for forming a coating film which may be added into the composition is used, a problem such as adhesiveness inhibition, contamination, and degradation of the cured film hardly occur because the silicone oil is fixed into the cured film of the curable composition of the invention by a chemical bond. In particular, it is more effective of enhancing adhesiveness to a deposited layer during a deposition process. In the case of a modified silicone which is modified with a functional group having a photocurability such as a (meth)acryloyl-modified silicone oil and a vinyl-modified silicone oil, the composition after cured are excellent in various properties because of cross-link with an ingredient of the curable composition of the invention.

The polysiloxane having trimethylsiloxysilicate is preferred because it easily bleeds out on surface thereof, thereby being excellent in peelability, it is also excellent in adhesiveness even if it bleeds out on surface thereof, and it is excellent in adhesiveness to a metal-deposited layer and an over coating layer.

Two or more of the release agents may be added in combination.

When the release agent is added into the curable composition of the invention, the amount to be added is preferably from 0.001 to 10% by mass of the total amount of the composition of the invention, more preferably from 0.01 to 5% by mass. When the amount to be added of the release agent falls into the range of from 0.01 to 5% by mass, the effect of peelability between a mold and a layer of the curable composition is enhanced, and roughness of the coating surface due to cissing is suppressed, adhesiveness of a substrate or a layer adjacent to the substrate, such as a deposition layer is inhibited, and fracture of coating film in transfer is suppressed to occur (becoming too weak in the strength of the film).

The curable composition of the invention may comprise an organic metal coupling agent in order to enhance heat resistance of the surface structure having a micropattern comprising recesses and projections, strength of the surface structure having a micro pattern comprising recesses and projections, or adhesiveness to a metal-deposited film. In addition, the organic metal coupling agent is effective from the viewpoint of promotion of a thermal-curing reaction. Examples of the organic metal coupling agent for use in the invention include a silane coupling agent, a titanium coupling agent, a zirconium coupling agent, an aluminium coupling agent, and a tin coupling agent.

The silane coupling agent for use in the curable composition of the invention includes, for example, vinylsilanes such as vinyltrichlorosilane, vinyltris(β-methoxyethoxy)silane, vinyltriethoxysilane, vinyltrimethoxysilane, etc.; epoxysilanes such as β-(3,4-epoxycyclohexyl)ethyltrimethoxysilane, γ-glycidoxypropyltrimethoxysilane, γ-glycidoxypropylmethyldiethoxysilane, etc.; aminosilanes such as N-β-(aminoethyl)-γ-aminopropyltrimethoxysilane, N-β-(aminoethyl)-γ-aminopropylmethyldimethoxysilane, γ-aminopropyltrimethoxysilane, N-phenyl-γ-aminopropyltrimethoxysilane, etc.; and other silane coupling agents such as γ-mercaptopropyltrimethoxysilane, γ-chloropropylmethyldimethoxysilane, γ-chloropropylmethyldiethoxysilane, etc.

The titanium coupling agent includes, for example, isopropyltriisostearoyl titanate, isopropyltridecylbenzenesulfonyl titanate, isopropyltris(dioctylpyrophosphate)titanate, tetraisopropylbis(dioctylphosphite)titanate, tetraoctylbis(ditridecylphosphite)titanate, tetra(2,2-diallyloxymethyl)bis (ditridecyl)phosphite titanate, bis(dioctylpyrophosphate) oxyacetate titanate, bis(dioctylpyrophosphate)ethylene titanate, isopropyltrioctanoyl titanate, isopropyldimethacrylisostearoyl titanate, isopropylisostearoyldiacryl titanate, isopropyltri(dioctylphosphate)titanate, isopropyltricumyl titanate, isopropyltri(N-aminoethyl-aminoethyl)titanate, dicumylphenyloxyacetate titanate, diisostearoylethylene titanate, etc.

The zirconium coupling agent includes, for example, tetra-n-propoxy zirconium, tetra-butoxy zirconium, zirconium tetraacetylacetate, zirconium dibutoxybis(acetylacetonate), zirconium tributoxyethyl acetacetate, zirconium butoxyacetylacetonate bis(ethylacetacetate), etc.

The aluminium coupling agent includes, for example, aluminium isopropylate, mono-sec-butoxyaluminium diisopropylate, aluminium sec-butyrate, aluminium ethylate, ethylacetacetate aluminium diisopropylate, aluminium tris (ethylacetacetate), alkylacetacetate aluminium diisopropylate, aluminium monoacetylacetonate bis(ethylacetacetate), aluminium tris(acetylacetate), etc.

The organic metal coupling agent may be added in an amount of from 0.001 to 10% by mass of the total solid ingredient of the curable composition of the invention. By adjusting the amount to be added of the organic metal coupling agent to 0.001% by mass or more, there is tendency to be more effective for enhancing the heat resistance, the strength, and the adhesiveness to a deposited layer. By adjusting the amount to be added of the organic metal coupling agent to 10% by mass or less, there is tendency to enhance the stability of the composition and to suppress failure of the formed film.

A polymerization inhibitor may be incorporated in the curable composition of the invention for the purpose of enhancing the storage stability of the composition. The polymerization inhibitor includes, for example, phenols such as hydroquinone, tert-butylhydroquinone, catechol, hydroquinone monomethyl ether; quinones such as benzoquinone, diphenylbenzoquinone; phenothiazines; cupper compounds, etc. Preferably, the polymerization inhibitor is incorporated in the curable composition optionally in an amount of from 0.001 to 10% by mass of the entire amount of the composition.

The curable composition of the invention may comprise an ultraviolet absorber.

Examples of commercial products of an ultraviolet absorber include Tinuvin P, and 234, 320, 326, 327, 328 and 213 (the above are manufactured by Ciba-Geigy), and Sumisorb110, 130, 140, 220, 250, 300, 320, 340, 350, and 400 (the above are manufactured by Sumitomo Chemical Co., Ltd.). The ultraviolet absorber is preferably added at the ratio of 0.01 to 10% by mass, relative to the total amount of the curable composition of the invention.

Examples of commercial products of a light stabilizer include Tinuvin 292, 144, 622LD (the above are manufactured by Ciba-Geigy), Sanol LS-770, 765, 292, 2626, 1114, and 744 (the above are manufactured by Sankyo Chemical Industries).

The light stabilizer is preferably added at the ratio of 0.01 to 10% by mass, relative to the total amount of the curable composition.

The curable composition may comprise an antiaging agent.

Examples of commercial products of an antiaging agent include Antigene W, S, P, 3C, 6C, RD-G, FR, and AW (the above are manufactured by Sumitomo Chemical Co., Ltd.).

The antiaging agent is preferably added at the ratio of 0.01 to 10% by mass, relative to the total amount of the curable composition.

The curable composition of the invention may comprise a plasticizer for the purpose of adjusting the adhesiveness to a substrate, the film pliability, the hardness. Preferred examples of the plasticizer include dioctylphthalate, didodecylphthalate, trimethyleneglycoldicaproate, dimethylglycolphthalate, tricresylphosphate, dioctyladipate, dibutylsebacate, triacetyladipate, dimethyladipate, diethyladipate, di(n-butyl)adipate, dimetylsuberate, diethylsuberate, and di(n-butyl)suberate. The plasticizer may be arbitrarily added in an amount of 30% by mass or less in the composition, preferably 20% by mass or less, more preferably 10% by mass. In order to ensure the addition effect of the plasticizer, the amount to be added is preferably 0.1% by mass.

The curable composition of the invention may comprise an adhesion promoter for the purpose of adjusting the adhesiveness to a substrate.

Examples of the an adhesion promoter for use in the invention include benzimidazoles, poly benzimidazoles, a pyridine derivative substituted with a lower hydroxyalkyl group, a nitrogen-containing hetero ring compound, urea or thiourea, an organic phosphorus compound, 8-oxyquinoline, 4-hydroxypteridine, 1,10-phenanthroline, 2,2'-bipyridine derivative, a benzotriazole, a phenylenediamine compound, 2-amino-1-phenylethanol, N-phenylethanolamine, N-ethyldiethanolamine, N-ethyldiethanol amine, N-ethyl ethanolamine and a derivative thereof, and a benzothiazole derivative.

The adhesion promoter is preferably added in the amount of 20% by mass or less, more preferably 10% by mass or less, further more preferably 5% by mass or less. In order to ensure a more effect, the amount to be added is preferably 0.1% by mass.

When the curable composition of the invention is cured, a thermal polymerization initiator may also be added if desired. Preferred examples of the thermal polymerization initiator include peroxide and an azo compound, specifically benzoyl peroxide, and tert-buthyl-peroxybenzoate, azobisisobutyronitrile. The content of the thermal polymerization initiator is preferably 5% by mass or less, more preferably 2% by mass or less, further preferably 1% by mass or less. In order to obtain the effect of addition of the thermal polymerization initiator, the content is preferably 1% by mass or more.

The curable composition of the invention may comprise a photobase generator for the purpose of adjusting a pattern form, sensitivity, etc. Examples of the photobase generator include 2-nitroglycerinebenzylcyclohexyl carbamate, triphenylmethanol, O-carbamoylhydroxyamide, O-carbamoyloxime, [[(2,6-dinitrobenzyl)oxy]carbonyl]cyclohexylamine, bis [[(2-nitrobenzyl)oxy]carbonyl]hexane 1,6-diamine, 4-(methylthiobenzoyl)-1-methyl 1-zimethyl aminoprophane, N-(2-nitrobenzyloxycarbonyl)pyrrolidine, hexaamminecobalt (III)tris(triphenylmethylborate), 2-benzyl-2-dimethylamino-1-(4-morpholinophenyl)-butanone, 2,6-dimethyl 3,5-diacetyl-4-(2'-nitroohenyl)-1,4-dihydropyridine, 2,6-dimethyl-3,5-diacetyl-4-(2',4'-dinitrophenyl)-1,4-dihydro pyridine.

The composition of the invention may comprise a colorant for the purpose of improving the visibility of a coating film. As the colorant, a pigment or a dye which is used for a composition for UV ink-jet, a composition for color filters, a composition for CCD image sensor may be used without deviating from the object of the invention.

The pigment for use in the invention is preferably those disclosed in JP-A-2008-105414, [0121]. The colorant is preferably added in an amount of from 0.001 to 2% by mass, relative to the total amount of the composition.

The curable composition of the invention may comprise elastomer particles for the purpose of improving the mechanical strength and the pliability.

The elastomer particles which may be added in the curable composition as an arbitrary ingredient have an average particle size of from 10 to 700 nm, more preferably from 30 to 300 nm. Examples thereof include elastomner particles of polybutadiene, polyisoprene, butadiene/acrylonitrile copolymer, styrene/butadiene copolymer, styrene/isoprene copolymer, ethylene/propylene copolymer, ethylene/alpha-olefin copolymers, ethylene/alpha-olefin/polyene copolymer, acrylic rubber, butadiene/(meth)acrylic ester copolymer, styrene/butadiene block copolymer, or styrene/isoprene block copolymer. Further, core/shell type particles in which those elastomer particles are coated with a methylmethacrylate polymer, methylmethacrylate/glycidylmethacrylate, or the like may be used. The elastomer particles may have a crosslink structure.

Examples of commercial products of the elastomer particles include Resinous Bond RKB (manufactured by Resinous Chemicals), and Techno MBS-61, MBS-69 (the above are manufactured by Techno polymer Co., Ltd.).

The elastomer particles are used singly or in combination of two or more kinds thereof. The amount of the elastomer to be added in the curable composition of the invention is preferably from 1 to 35% by mass, more preferably from 2 to 30% by mass, further more preferably from 3 to 20% by mass.

The curable composition of the invention may comprise a basic compound arbitrarily for the purpose of suppressing the cure shrinkage and of improving the heat stability. Examples of the basic compound include an amine, a nitrogen-containing hetero ring compound such as quinoline and quinolizine, a basic alkali metal compound, and a basic alkaline-earth-metals compound. Of those, preferred is an amine from the viewpoint of the compatibility with a polymerizable monomer, and examples of the amine include octylamine, naphthylamine, xylenediamine, benzylamine, diphenylamine, dibutylamine, dioctylamine, dimethylaniline, quinuclidine, tributylamine, trioctylamine, tetramethylethylenediamine, tetramethyl-1,6-hexamethylenediamine, hexamethylenetetramine, and triethanolamine.

The composition of the invention may comprise a chain transfer agent for the purpose of improving the photocurability.

Examples thereof include 4-bis(3-mercaptobutyryloxy) butane, 1,3,5-tris(3-mercaptobutyryloxyethyl) 1,3,5-triazine-2,4,6(1H,3H,5H)-trione, and pentaerythritoltetrakis(3-mercaptobutyrate).

The curable composition of the invention preferably comprises water in an amount of 2.0% by mass or less at the time of the preparation of the composition, preferably 1.5% by mass or less, more preferably 1.0% by mass. By adjusting the amount of water at the time of the preparation to 2.0% by mass or less, the preservability of the curable composition of the invention becomes more stability.

The curable composition for nanoimprints of the invention may comprise a solvent, preferably is a substantively solventless type composition. The "substantively solventless type composition" herein means a composition which does not substantively comprise any organic solvent. Specifically, in the curable composition of the invention, the content of an organic solvent is 3% by mass or less. Since the composition of the invention may comprise monofunctional or difunctional polymerizable monomer as a reactive diluent, the composition does not necessarily comprise an organic solvent for dissolving ingredients in the composition of the invention. When the composition does not comprise an organic solvent, there is no need for a baking step for the purpose of volatilizing solvents, and therefore, there is more advantageous merit such as effective simplification of process. Therefore, in the curable composition of the invention, the content of the organic solvent is preferably 3% by mass or less, more preferably 2% by mass or less, furthermore preferably 0% by mass. As thus-mentioned, the curable composition of the invention does not necessarily comprise an organic solvent. However, an organic solvent may be arbitrarily added in the case where a compound which can not dissolve in the reactive diluent is dissolved in the curable composition of the invention, or in the case where the viscosity of the curable composition is need to be slightly adjusted. The organic solvent preferably used in the curable composition of the invention is not specifically limited as far as the solvent is generally used in a curable composition for photoimprints or in photoresist, can dissolve and uniformly disperse the compound used in the invention, and does not react with another ingredient in the composition.

Examples of the organic solvent include solvents disclosed in JP-A-H2008-105414, paragraph 0088.

One of more kinds of the organic solvents may be used. In the invention, the organic solvent is preferably methoxy propylene glycol acetate, 2-hydroxy propionic acid ethyl, 3-methoxy propionic acid methyl, 3-ethoxy propionic acid ethyl, ethyl lactate, cyclohexanone, methyl isobutyl ketone and 2-heptanone, etc.

[Curable Composition for Nanoimprints]

The curable composition of the invention may be used as a curable composition for nanoimprints according to photonanoimprint methods. Hereinunder, "the curable composition of the invention and the like" means both of the curable composition and the curable composition for nanoimprints of the invention.

Generally, the curable composition used for the photonanoimprint method comprises a photopolymerization initiator which starts a polymerization reaction of the polymerizable monomer through photo irradiation, a surfactant and an antioxidant, if necessary, in addition to the polymerizable monomer comprising a polymerizable functional group. Since the curable composition for nanoimprints of the invention comprises the aromatic carbonic alkenyl ester represented by the above formula (1) as the above polymerizable monomer, which may be sometimes referred to as "the aromatic carbonic acid alkenyl ester in the invention", the cured products formed by using the curable composition of the invention are excellent in patterning ability of micropattern comprising recesses and projections (patterning accuracy), light transmittance, releasability from a mold (there is less residual of the composition on the mold), and the cured composition has high curability. The cured products formed by using the curable composition for nanoimprints of the invention (pattern) has good light transmittance after cured (for example, the composition is heated and cured at 200° C. or higher). The curable composition and the like can be comprehensively excellent in various coating properties such as coatability and other productivity. Thus, the curable composition for nanoimprints of the invention can be widely applied to fields applicable to photonanoimprint lithography.

Thus, the curable composition and the curable composition for nanoimprints of the invention can have the following features.

(1) As excellent in solution flowability at room temperature, the composition can readily flow into the cavity of the recesses part of a mold and hardly takes air therein to cause bubble defects; and after photo-cured, the composition leaves few residues in both the recesses and the projections of a mold.

(2) After cured, the cured film is excellent in mechanical properties, adhesiveness between the coating film and the substrate, and releasability of the coating film from a mold. Therefore, when the cured film is peeled away from a mold, it is free from troubles of pattern deformation or coating film surface stringiness to cause surface roughness, and the cured film may form a good pattern (good patterning accuracy).

(3) As excellent in coating uniformity, the composition is suitable to the filed of application to large-size substrates and micropatterning thereon.

(4)The composition is excellent in light transmittance, residual membrane performance, mechanical performance such as scratched resistance (curability), and solvent resistance, the composition is preferably used for various permanent films.

Thus, the curable composition and the curable composition for nanoimprints of the invention are favorably applied to semiconductor integrated circuits and components of liquid-crystal display devices (especially to microfabrication for thin-film transistors of liquid-crystal displays, protective films of liquid-crystal color filters, spacers and other components of liquid-crystal display devices, etc.) to which, however, conventional compositions are heretofore difficult to apply; and in addition, the composition of the invention is further applicable to production of any others, widely for example, partitioning materials for plasma display panels, flat screens, microelectromechanical systems (MEMS), sensor devices, optical discs, magnetic-recording media such as high-density memory discs, optical parts such as diffraction gratings and relief holograms, nanodevices, optical devices, optical films, polarization devices, organic transistors, color filters, overcoat layers, pillar materials, rib materials for liquid-crystal alignment, microlens arrays, immunoassay chips, DNA separation chips, microreactors, nanobio devices, optical waveguides, optical filters, photonic liquid crystals, etc.

Of the above fields, the cured products obtained by curing the curable composition for nanoimprints of the invention are excellent in light transmittance after photoirradiation, for example, after the composition is subjected to heat treatment at 200° C. or higher (post bake), and therefore, the composition is favorable for application to a permanent film which requires light transmittance property (for example, a protection film for liquid crystal color filters, a spacer).

(Viscosity of the Curable Composition of the Invention and the Like)

The viscosity of the curable composition and the curable composition for imprints of the invention are described. The viscosity of the invention is a viscosity at 25° C. unless specifically defined. The viscosity at 25° C. of the curable composition and the curable composition for nanoimprints of the invention are preferably 3 to 18 mPa·s, more preferably 5 to 15 mPa·s, further more preferably 7 to 12 mPa·s. By setting the viscosity of the composition to such a range, the curable composition can obtain various appropriate fabrication performances such as forming performance of micropattern having projections and recesses, coatability or the like before cured, and the curable composition can obtain various excellent performances of a coated film for resolution, line edge roughness property, residual property and adhesiveness to a substrate and other points. It is not good that the viscosity of the curable composition and the curable composition for imprints and the curable composition for nanoimprints of the invention is merely low. Specifically, when the viscosity of the photocurable composition of the invention is less than 3 mPa·s, then the composition may cause a problem of coating failure on substrates and a problem that the mechanical strength of the coating film may be weak. Concretely, it is bad that the viscosity is too low because coating unevenness occurs in coating the composition and the composition flows out on substrate in application thereto. On the other hand, when the viscosity of the photocurable composition and the curable composition for nanoimprints is more than 18 mPa·s, the following problems maybe caused. When a mold having a micropattern having projections and recesses is airtightly attached to the photocurable composition, the composition may hardly flow into the cavity of the projection part of the mold, and take bubbles therein, and therefore, the composition may cause a problem of bubble defects and, after cured, the composition easily leaves residues in the projection part of the mold. The composition for photonanoimprint which has been disclosed in Resist Material Hand Book, P1, 103 to 104 (2005, Johokiko Pulbication) or the like has a viscosity of about 50 mPa·s, and therefore, there is a problem of bubble defects and residual in recesses of a mold after photo-cured, and the composition is only applicable to limited use.

In general, the viscosity of the curable composition may be controlled by blending various monomers, oligomers and polymers having a different viscosity. For planning the viscosity of the curable composition and the curable composition for nanoimprints of the invention so as to fall within the above-mentioned range, preferably, a monomer compound having a viscosity of 10 mPa·s or less is added to control the viscosity of the composition.

[Method for Manufacturing Cured Product]

The method for manufacturing a curd product (especially, a micropattern comprising recesses and projections) of using the curable composition of the invention and the like is described below. The method for manufacturing a curd product of the invention comprises applying the curable composition of the invention onto a substrate or a support (base) to form a patterning layer thereon; pressing a mold against the surface of the patterning layer; and irradiating the patterning layer with light, thereby curing the composition of the invention to form a micropattern. Especially, it is preferable that the curable composition of the invention is, after being irradiated with light, further heated and cured in order to enhance degree of curability for the cured product.

The cured product obtained by the method for producing a cured product of the invention is excellent in pattern transfer accuracy, curability and light transmittance, and is preferably applicable to a protection film for liquid crystal color filters, a spacer, and other components for liquid crystal displays.

Concretely, the patterning layer comprising at least the curable composition of the invention and the like is applied onto a substrate (base or support) and optionally dried to form a layer comprising the curable composition of the invention and the like (patterning layer), thereby preparing a pattern acceptor (having the patterning layer formed on the substrate), then a mold is pressed against the surface of the patterning layer of the pattern acceptor to thereby transfer the mold pattern, and the micropatterned layer is cured through photoirradiation and heating. The photoirradiation and heating may be carried out over times. The photoimprint lithography (the method for manucafcutring the cured product) by the patterning method of the invention may enable lamination and multi-layer patterning, and therefore, may be used in combination with an ordinary thermoimprint.

The curable composition for nanoimprints of the invention may form a finer micropattern at low cost and with high accuracy by a photonanoimprint method. Accordingly, the composition of the invention can form micropatterns heretofore formed by conventional photolithography technology at low cost and with high accuracy. For example, when the composition of the invention is applied onto a substrate or a support, and the layer comprising the composition is exposed to light, cured, and optionally dried (baked), it thus can be employed as a permanent film of an overcoat layer or an insulating film, and the like for use in liquid-crystal displays (LCD); and the like, and as an etching resist for semiconductor integrated circuits, recording materials, flat panel displays, or the like. In particular, the patterns formed by using the curable composition for nanoimprints of the invention are excellent in etching property, and can be preferably used as an etching resist in dry etching using fluorocarbon, etc. Since the curable composition for nanoimprints of the invention is excellent in light transmittance after cured, a permanent film such as an overcoat layer and an insulation film can be formed.

In the permanent films (resists for structural members) for use in liquid-crystal displays (LCD) and in fabrication of a substrate for electronic materials, the resist is preferably prevented from being contaminated as much as possible with metallic or organic ionic impurities in order that the resist does not interfere with the performance of the displays. The concentration of the metallic or organic ionic impurities in the curable composition of the invention is preferably at most 1000 ppm, more preferably at most 100 ppm, and furthermore preferably at most 10 ppb.

The method for manufacturing a cured product using the curing composition of the invention (the patterning method (pattern transferring method)) is described concretely hereinunder.

The coating method for applying the curable composition for nanoimprints of the invention onto a substrate may be a well known coating method of, for example, a dip coating method, an air knife coating method, a curtain coating method, a wire bar coating method, a gravure coating method, an extrusion coating method, a spin coating method, a slit scanning method, an inkjet method, etc. The thickness of the patterning method of the composition of the invention may vary depending on the use thereof, and may be from 0.05 μm to 30 μm or so. The composition of the invention may be applied in a mode of multilayer coating. Between the substrate and the patterning method of the composition of the invention, any other organic layer may be formed, such as a planarizing layer, an adhesive layer, etc. With that, the patterning layer is not kept in direct contact with the substrate, and therefore, the substrate may be prevented from being contaminated with dust or from being scratched and the adhesiveness between the pattering layer and the substrate is enhanced. The pattern to be formed of the composition of the invention may have good adhesiveness to the organic layer, if any, formed on the substrate.

The substrate (base or support) to which the curable composition for nanoimprints of the invention is applied may be selected from various materials depending on its use, including, for example, quartz, glass, optical film, ceramic material, vapor deposition film, magnetic film, reflective film, metal substrate of Ni, Cu, Cr, Fe or the like, paper, SOG (spin on glass), polymer substrate such as polyester film, polycarbonate film or polyimide film, TFT array substrate, PDP electrode plate, glass or transparent plastic substrate, electroconductive substrate of ITO, metal or the like, insulating substrate, semiconductor substrate such as silicon, silicon nitride, polysilicon, silicon oxide or amorphous silicon, which, however, are not limitative. The shape of the substrate is not also specifically defined. It may be tabular or roll. As described below, the substrate may be light-transmissive or non-light-transmissive, depending on the combination thereof with a mold.

Next, in the patterning method of the invention, a mold is pressed against the surface of the patterning layer for transferring the pattern from the mold onto the patterning layer. Accordingly, the micropattern previously formed on the pressing surface of the mold is transferred onto the patterning layer.

The mold material usable in the invention is described. In the photoimprint lithography with the composition of the invention, a light-transmissive material is selected for at least one of the mold material and/or the substrate. In the photoimprint lithography applied to the invention, the curable composition for nanoimprints of the invention is applied onto a substrate to form a patterning layer thereon, and a light-transmissive mold is pressed against the surface of the layer, then this is irradiated with light from the back of the mold and the patterning layer is thereby cured. Alternatively, the curable composition for photoimprints is applied onto a light-transmissive substrate, then a mold is pressed against it, and this is irradiated with light from the back of the substrate whereby the curable composition for photoimprints can be cured.

The photoirradiation may be attained while the mold is kept in contact with the layer or after the mold is released. In the invention, preferably, the photoirradiation is attained while the mold is kept in contact with the patterning layer.

The mold usable in the invention has a transferable pattern formed thereon. The pattern of the mold may be formed, for example, through photolithography, electronic beam lithography or the like by which a pattern may be formed to a desired processing accuracy. In the invention, however, the mold patterning method is not specifically defined.

Not specifically defined, the light-transmissive mold material for use in the invention may be any one having a desired strength and durability. Concretely, its examples include glass, quartz, light-transparent resin such as PMMA or polycarbonate resin, transparent metal deposition film, flexible film of polydimethylsiloxane or the like, photo-cured film, metal film, etc.

The non-light-transmissive mold to be used in the invention where a light-transmissive substrate is used is not also specifically defined and may be any one having a predetermined strength. Concretely, examples of the mold material include ceramic material, deposition film, magnetic film, reflective film, metal material of Ni, Cu, Cr, Fe or the like, as well as SiC, silicon, silicon nitride, polysilicon, silicon oxide, amorphous silicon, etc. However, these are not limitative. The shape of the mold is not also specifically defined, and may be any of a tabular mold or a roll mold. The roll mold is used especially when continuous transfer in patterning is desired.

The mold for use in the patterning method of the invention may be processed for surface release treatment for the purpose of enhancing the releasability of the curable composition for nanoimprint of the invention from the mold. The mold of the type includes those surface-treated with a silicone-type or fluorine-containing silane coupling agent, for which, for example, commercial release agents such as Daikin's Optool DSX, Sumitomo 3M's Novec EGC-1720 and others are preferred.

In photonanoimprint lithography with the composition of the invention, in general, the mold pressure in the patterning method of the invention is preferably at most 10 atmospheres. When the mold pressure is at most 10 atmospheres, then the mold and the substrate are hardly deformed and the patterning accuracy tends to increase. It is also favorable since the pressure unit may be small-sized since the pressure to be given to the mold may be low. The mold pressure is preferably selected from the region capable of securing the mold transfer uniformity, within a range within which the residual film of the curable composition for nanoimprints in the area of mold pattern projections may be reduced.

In the patterning method of the invention, the dose of photoirradiation in the step of irradiating the patterning layer with light maybe sufficiently larger than the dose necessary for curing. The dose necessary for curing maybe suitably determined depending on the degree of consumption of the unsaturated bonds in the curable composition for nanoimprints and on the tackiness of the cured film as previously determined.

In the photoimprint lithography applied to the invention, the substrate temperature in photoirradiation may be room temperature; however, the photoirradiation may be attained under heat for enhancing the reactivity. In the previous stage of photoirradiation, preferably, the system is kept in vacuum as effective for preventing contamination with bubbles or contamination with oxygen or for preventing the reduction in reactivity, and as effective for enhancing the adhesiveness of the curable composition for nanoimprints with mold. The system maybe subjected to photoirradiation while still kept in vacuum. In the patterning method of the invention, the vacuum degree in photoirradiation is preferably from $10^{-1}$ Pa to ordinary pressure.

Light to be used for photoirradiation to cure the curable composition for nanoimprints of the invention is not specifically defined. For example, it includes light and irradiations with a wavelength falling within a range of high-energy ionizing radiation, near-ultraviolet, far-ultraviolet, visible, infrared, etc. The high-energy ionizing radiation source includes, for example, accelerators such as Cockcroft accelerator, Handegraf accelerator, linear accelerator, betatoron, cyclotron, etc. The electron beams accelerated by such an accelerator are used most conveniently and most economically; but also are any other radioisotopes and other radiations from nuclear reactors, such as γ rays, X rays, α rays, neutron beams, proton beams, etc. The UV sources include, for example, UV fluorescent lamp, low-pressure mercury lamp, high-pressure mercury lamp, ultra-high-pressure mercury lamp, xenon lamp, carbon arc lamp, solar lamp, etc. The radiations include microwaves, EUV, etc. In addition, laser rays for use in microprocessing of semiconductors, such as LED, semiconductor laser ray, 248 nm KrF excimer laser ray, 193 nm ArF excimer laser ray and others, are also favorably used in the invention. These lights may be monochromatic lights, or may also be lights of different wavelengths (mixed lights).

In photoexposure, the light intensity is preferably within a range of from 1 mW/cm$^2$ to 50 mW/cm$^2$. When the light intensity is at least 1 mW/cm$^2$, then the producibility may increase since the photoexposure time may be reduced; and when the light intensity is at most 50 mW/cm$^2$, then it is favorable since the properties of the permanent film formed may be prevented from being degraded owing to side reaction. Also preferably, the dose in photoexposure is within a range of from 5 mJ/cm$^2$ to 1000 mJ/cm$^2$ since the photoexposure margin is wide, the photocuring is sufficient and the unreacted matter hardly adheres to mold. In addition, the composition hardly decomposes and the permanent film formed is hardly degraded.

Further, in photoexposure, the oxygen concentration in the atmosphere may be controlled to be less than 100 mg/L by introducing an inert gas such as nitrogen or argon into the system for preventing the radical polymerization from being retarded by oxygen.

In the patterning method of the invention, after the pattern layer is cured through photoirradiation, if desired, the cured pattern may be further cured under heat given thereto(post-bake step). The heating maybe carried out before or after the pattern layer after photoirradiation is peeled from the mold. Thermal curing of the composition of the invention after photoirradiation is preferably attained at 150 to 280° C., more preferably at 200 to 250° C. The heating time is preferably from 5 to 60 minutes, more preferably from 15 to 45 minutes.

The cured product of the invention formed by the patterning method of the invention is also useful as an etching resist. In cases where the curable composition for nanoimprints of the invention is used as an etching resist, a nano-order micropattern is first formed on a substrate such as a silicon wafer with a thin film of $SiO_2$ or the like formed thereon, according to the patterning method of the invention. Next, by etching it with an etching gas, such as hydrogen fluoride, or the like in case of wet etching or $CF_4$, or the like in case of dry etching, a desired pattern can be formed on the substrate. The curable composition for nanoimprints is particularly excellent in resistance to dry etching.

The curable composition of the invention may be prepared by mixing the above-mentioned ingredients and, then, filtering it through a filter having a pore size of from 0.05 μm to 5.0 μm to give a solution. In the case of a curable composition for photonanoimprint lithography, mixture and dissolution is carried out at a temperature range of from 0° C. to 100° C. The filtration maybe effected in plural stages, or maybe repeated plural times. The solution once filtered may be again filtered. Not specifically defined, the material of the filter may be any one, for example, polyethylene resin, polypropylene resin, fluororesin, nylon resin, etc.

The pattern thus formed according to the patterning method of the cured product of the invention as described in the above can be used as a permanent film (a resist for a structural member) for use in liquid-crystal displays (LCD) and others, or as an etching resist. After its production, the permanent film may be bottled in a container such as a gallon bottle or a coated bottle, and may be transported or stored. In this case, the container may be purged with an inert gas such as nitrogen, argon or the like for preventing the composition therein from being degraded. The composition may be transported or stored at ordinary temperature, but for preventing the permanent film from being degraded, it is preferably transported or stored at a controlled temperature of from −20° C. to 0° C. Needless-to-say, the composition is shielded from light to such a level on which its reaction does not go on.

EXAMPLES

The characteristics of the invention are described more concretely with reference to Production Examples and Examples given below. In the following Examples, the material used, its amount and the ratio, the details of the treatment and the treatment process may be suitably modified or changed not overstepping the scope of the invention. Accordingly, the invention should not be limitatively interpreted by the Examples mentioned below.

[Synthesis of (Meth)acrylate Compound Represented by the Formula (1) of the Invention]

(Synthesis of Exemplified Compound M-1)

To a mixture solution of 4-hydroxybenzonic acid (55 g), potassium carbonate (110 g) and N-methyl pyrolidone (500 ml), aryl bromide (48 g) was added and reacted 60° C. After disappearance of the raw materials was confirmed with thin-layer chromatography, the reaction solution was cooled to 25° C. To the reaction solution, acrylic chloride (40 ml) was added and reacted at 50° C. After disappearance of the raw materials was confirmed, water (700 ml) and ethyl acetate (700 ml) was added for extraction. The organic layer was wished twice with 1 N of hydrochloric acid aqueous solution (500 ml), wished once with saturated saline, and then, the organic layer was condensed to obtain crude of the compound M-1. 99 g of the compound M-1 was obtained by purifying the crude through silica-gel chromatography. Its 1H-NMR data was shown below.

1H-NMR (300 MHz, CDCl3) δ: 4.8 (d, 2H), 5.3 (d, 1H), 5.4 (d, 1H), 6.0 (m, 2H), 6.3 (dd, 1H), 6.6 (d, 1H), 7.2 (d, 2H), 8.2 (d, 2H)

(Synthesis of Exemplified Compound M-2)

The compound M-2 was synthesized by the same method as that in the exemplified compound M-1, except that 4-hydroxybenzonic acid was replaced with 3-hydroxybenzonic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 2H), 5.3 (d, 1H), 5.4 (d, 1H), 6.0 (m, 2H), 6.3 (dd, 1H), 6.4 (d, 1H), 7.3 (d, 1H), 7.5 (dd, 1H), 7.8 (s, 1H), 8.0 (d, 1H)

(Synthesis of Exemplified Compound M-3)

The compound M-3 was synthesized by the same method as that in the exemplified compound M-1, except that 4-hydroxybenzonic acid was replaced with salicylic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 2H), 5.2 (d, 1H), 5.4 (d, 1H), 6.0 (dt, 1H), 6.1 (d, 1H), 6.4 (dd, 1H), 6.5 (d, 1H), 7.3 (d, 1H), 7.4 (dd, 1H), 7.7 (dd, 1H), 8.0 (d, 1H)

emplified Compound M-4)

The compound M-4 was synthesized by the same method as that in the exemplified compound M-1, except that 4-hydroxybenzonic acid was replaced with 5-hydroxyisophthalic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 4H), 5.3 (d, 2H), 5.4 (d, 2H), 6.1 (m, 3H), 6.5 (dd, 1H), 6.6 (d, 1H), 8.0 (s, 2H), 8.6 (s, 1H)

(Synthesis of Exemplified Compound M-5)

The compound M-5 was synthesized by the same method as that in the exemplified compound M-1, except that 4-hydroxybenzonic acid was replaced with 3, 5-dihydroxybenzonic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 2H), 5.3 (d, 1H), 5.4 (d, 1H), 6.0 (m, 3H), 6.3 (dd, 2H), 6.6 (d, 2H), 7.2 (s, 1H), 7.7 (s, 1H)

(Synthesis of Exemplified Compound M-6)

The compound M-6 was synthesized by the same method as that in the exemplified compound M-1, except that 4-hydroxybenzonic acid was replaced with 2-hydroxy-1-naphthoic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 2H), 5.1 (d, 1H), 5.4 (d, 1H), 6.1 (m, 3H), 6.4 (dd, 1H), 6.6 (d, 1H), 7.4 (d, 1H), 7.6 (m, 2H), 8.0-8.2 (m, 3H)

(Synthesis of Exemplified Compound M-7)

The compound M-7 was synthesized by the same method as that in the exemplified compound M-1, except that 4-hydroxybenzonic acid was replaced with 6-hydroxy-2-naphthoic acid as the raw material, and the contents of potassium carbonate, aryl bromide and acrylic chloride were appropriately adjusted. Its 1H-NMR data was shown below.

1H-NMR(300 MHz, CDCl3) δ: 4.8 (d, 2H), 5.3 (d, 1H), 5.4 (d, 1H), 6.4 (dd,1H), 6.7 (d, 1H), 7.1 (m, 2H), 7.5 (d, 1H), 7.7 (d, 1H), 7.9 (d, 1H), 8.4 (s, 1H)

(Synthesis of Exemplified Compound M-9)

The compound M-9 was synthesized by the same method as that in the exemplified compound M-1, except that acrylic chloride was replaced with methacrylic chloride. Its 1H-NMR data was shown below.

1H-NMR(300 MHz, CDCl3) δ: 2.8 (s, 3H), 4.8 (d, 2H), 5.3 (d, 1H), 5.4 (d, 1H), 6.0 (dt, 1H), 6.1 (d, 1H), 6.6 (d, 1H), 7.2 (d, 2H), 8.2 (d, 2H)

Preparation of Curable Composition

Examples 1 to 9, Comparative Examples 1 and 2

The curable composition was prepared by adding the following photopolymerization initiator P-1, the following surfactants W-1 and W-2, and the following antioxidant A-1 and A-2 into the above exemplified compounds of the (meth) acrylate compound represented by the formula (1) of the invention and the following other polymerizable compounds (functional monomer) according to the composition shown in the following tables 1 to 3.

<Other Monofunctional Monomers>

R-1: benzyl acrylate (Biscoat #160, manufactured by Osaka Organic Chemical Industry Ltd.)

R-2: ethyl oxetanyl ethyl acrylate (OXE-10: manufactured by Toagosei Co., Ltd.)

R-3: trimethoxysilyl propyl acrylate (KBM5103: manufactured by Shin-Etsu Chemical Co., Ltd.)

<Other Bifunctional Monomer>

S-01: neopentyl glycol diacrylate (KAYARD NPGDA: manufactured by Nipponkayaku)

<Other Tri or More-Functioal Monomer>

S-10: trimethylolpropane triacrylate (Aronix M-309, manufactured by Toagosei)

S-11: pentaerythritol tetraacrylate (manufactured by Ardrich)

<Photopolymerization Initiator>

P-1: 2,4,6-trimethylbenzoyl-ethoxy phenyl-phosphine oxide (Lucirin TPO-L, manufactured by BASF)

<Surfacatant>

W-1: fluorine series surfactant (manufactured by Tokem products: fluorine series surfactant)

W-2: silicone series surfactant (manufactured by DIC Corporation: Mefacaf paindant 31)

<Antioxidant>

A-1: Sumilizer GA80 (manufactured by Sumitomo Chemical Co., Ltd.)

A-2: Adecastab AO503 (manufactured by Adeka)

TABLE 1

| | Example 1 | | Example 2 | | Example 3 | | Example 4 | | Example 5 | |
|---|---|---|---|---|---|---|---|---|---|---|
| | Compound | % by mass | Compound | % by mass | Compound | % by mass | Compound | % by mass | Compound | % by mass |
| Polymerizable unsaturated monomer | M-1 | 17.2 | M-2 | 17.2 | M-4 | 17.2 | M-5 | 17.2 | M-6 | 17.2 |
| | R-1 | 23.3 | R-1 | 23.3 | R-1 | 23.3 | R-1 | 23.3 | R-1 | 23.3 |
| | R-2 | 23.2 | R-2 | 23.2 | R-2 | 23.2 | R-2 | 23.2 | R-2 | 23.2 |
| | R-3 | 10 | R-3 | 10 | R-3 | 10 | R-3 | 10 | R-3 | 10 |
| | S-10 | 22.4 | S-10 | 22.4 | S-10 | 22.4 | S-10 | 22.4 | S-10 | 22.4 |
| Photopolymerization initiator | P-1 | 0.5 | P-1 | 0.5 | P-1 | 0.5 | P-1 | 0.5 | P-1 | 0.5 |
| Surfactant | W-1 | 0.1 | W-1 | 0.1 | W-1 | 0.1 | W-1 | 0.1 | W-1 | 0.1 |
| | W-2 | 0.04 | W-2 | 0.04 | W-2 | 0.04 | W-2 | 0.04 | W-2 | 0.04 |
| Antioxidant | A-1 | 1 | A-1 | 1 | A-1 | 1 | A-1 | 1 | A-1 | 1 |
| | A-2 | 2 | A-2 | 2 | A-2 | 2 | A-2 | 2 | A-2 | 2 |

TABLE 2

| | Example 6 | | Example 7 | | Example 8 | | Example 9 | |
|---|---|---|---|---|---|---|---|---|
| | Compound | % by mass | Compound | % by mass | Compound | % by mass | Compound | % by mass |
| Polymerizable unsaturated monomer | M-7 | 17.2 | M-9 | 17.2 | M-1 | 20.2 | M-1 | 20.2 |
| | R-1 | 23.3 | R-1 | 23.3 | R-2 | 33.2 | R-1 | 23.3 |
| | R-2 | 23.2 | R-2 | 23.2 | R-3 | 10 | R-2 | 23.2 |
| | R-3 | 10 | R-3 | 10 | S-10 | 35.4 | R-3 | 10 |
| | S-10 | 22.4 | S-10 | 22.4 | | | S-10 | 22.4 |
| Photopolymerization initiator | P-1 | 0.5 | P-1 | 0.5 | P-1 | 0.5 | P-1 | 0.5 |
| Surfactant | W-1 | 0.1 | W-1 | 0.1 | W-1 | 0.1 | W-1 | 0.1 |
| | W-2 | 0.04 | W-2 | 0.04 | W-2 | 0.04 | W-2 | 0.04 |
| Antioxidant | A-1 | 1 | A-1 | 1 | | | | |
| | A-2 | 2 | A-2 | 2 | | | | |

TABLE 2-continued

| | Example 6 | | Example 7 | | Example 8 | | Example 9 | |
|---|---|---|---|---|---|---|---|---|
| | Compound | % by mass | Compound | % by mass | Compound | % by mass | Compound | % by mass |

TABLE 3

| | Comparative Example 1 | | Comparative Example 2 | |
|---|---|---|---|---|
| | Compound | % by mass | Compound | % by mass |
| Polymerizable unsaturated monomer | Light ester BZ | 57 | X-1 | 20.2 |
| | 1G | 9.5 | R-1 | 23.3 |
| | BPE-500 | 28.5 | R-2 | 23.2 |
| | | | R-3 | 10 |
| | | | S-10 | 22.4 |
| Photopolymerization initiator | Irgacure 907 | 4.9 | P-1 | 0.5 |
| Surfactant | Megafack R08 | 0.1 | W-1 | 0.1 |
| | | | W-2 | 0.04 |
| Antioxidant | | | | |

In Table 3, Comparative Example 1 corresponds to the photocurable composition in Example 2 in JP-A-2007-186570. In this, BPE-500 as a (meth)acrylate and 1G as an ethylene diglycol di(meth)acrylate is a polymerizable unsaturated monomer manufactured by Shin-Nakamura Chemical Co., Ltd., Light ester BZ as a benzyl(meth)acrylate is a polymerizable unsaturated monomer manufactured by Kyoeisha Chemical Co., Ltd., Irgacure 907 is a photopolymerization initiator manufactured by Ciba speciality chemicals Inc., and Megafac R08 is a surfactant manufactured by DIC Corporation.

The composition in Comparative Example 2 is the same composition as that in Example 9, except that the exemplified compound M-1 was replaced with X-1, which is a benzonate allyl ester disclosed in Examples 2 and 3 in JP-A-H10-251473.

[Evaluation of Curable Composition]

For Examples 1 to 9 and Comparative Examples 1 and 2, the viscosity, the pattern accuracy, the peelability, the surface hardness, the elastic recovery ratio and the solvent resistance were measured and evaluated according to the following evaluation methods.

<Measurement of Viscosity>

The measurement of the viscosity was conducted at 25±0.2° C. using a RE-80 L-type rotational viscometer manufactured by Toki Sangyo Co., Ltd. The measurement of the viscosity was conducted, respectively, by setting the rotation speed in the measurement at 100 rpm in the case of 0.5 mPa·s or more and less than 5 mPa·s, at 50 rpm in the case of 5 mPa·s or more and less than 10 mPa·s, at 20 rpm in the case of 10 mPa·s or more and less than 30 mPa·s, at 10 rpm in the case of 30 mPa·s or more and less than 60 mPa·s, at 5 rpm in the case of 60 mPa·s or more and less than 120 mPa·s, and at 1 rpm or 0.5 rpm in the case of 120 mPa·s or more. The results are shown in Table 4.

<Observation of Pattern Accuracy>

On a glass substrate, each of the compositions in each Examples and each Comparative Examples was coated by spin-coating to form a film having a thickness of 3.0 μm. The spin-coated film was pressed with a mold in a depressed chamber, and the pressure was retuned to atmosphere pressure with nitrogen gas. The substrate with the mold was moved to a box for expose, and exposed to a light source of a high-pressure mercury lamp (by ORC) (lamp power, 2000 mW/cm$^2$) at an expose amount of 240 mJ/cm$^2$ from the mold side under nitrogen atmosphere. After the expose, the mold was peeled therefrom to thereby obtain resist pattern. The obtained resist pattern was heated with an oven at 230° C. for 30 minutes, to thereby completely be cured.

Shape of the resist pattern after cured was observed using a scanning electromicroscope or an optical microscope. The pattern was classified and evaluated as follows;

A: A pattern is almost the same as the original pattern which forms a pattern of the mold.

B: A pattern has a different part from the original pattern which forms a pattern of the mold (in the range of less than 10%).

C: A pattern has a different part from the original pattern which forms a pattern of the mold (in the range of not less than 10% to less than 20%).

D: A pattern is completely different from the original pattern which forms a pattern of the mold, or has a different part from the original pattern which forms a pattern of the mold (in the range of not less than 20%).

<Evaluation of Peelability>

Using the same sample as that used in the observation of the pattern accuracy, the mold which was used in forming pattern was observed about whether the composition adheres to or not, with scanning electron microscope or light microscope, and the peelability was evaluated as follows:

A: No adhesion of the curable composition to the mold was observed.

B: Little adhesion of the curable composition to the mold was observed.

C: Adhesion of the curable composition to the mold was clearly observed.

<Evaluation of Surface Hardness>

On a glass substrate, each of the compositions in each Examples and each Comparative Examples was coated by spin-coating to form a film having a thickness of 3.0 μm, and exposed to a light source at an expose amount of 240 mJ/cm$^2$ under nitrogen atmosphere without pressing the mold, and heated with an oven at 230° C. for 30 minutes, to thereby be cured. The surface hardness of the cured film was evaluated with a pencil which was pressed at load power of 500 g.

Using the pencils each having hardness of from 1H to 6H, the hardness was evaluated for the six stages in that order. The contact surface of the pencil was observed with an optical microscope. The surface hardness was defined as follows:

Surface Hardness=(surface hardness upon starting observing a few or more lines on the surface) minus (1H). The highest surface hardness was evaluated as A, and the results are shown in the six stages from A to F.

<Elastic Recovery Ratio Evaluation>

A cured film was formed according to the same method as that in the surface hardness and evaluated. Trucking test was carried out with a microhardness testing machine manufactured by Shimadzu Corporation. The measuring condition was trigonal pyramid indenter at the load of 3 mN at the retention time of 1 second.

The elastic recovery ratio was defined and evaluated as follows:

Elastic Recovery Ratio={(Displacement at application of the highest load [μm])−(Return displacement at relaxation of the load [μm])}÷(Displacement at application of the highest load [μm])×100

A: 60% or more
B: from 50% or more to less than 60%
C: from 40% or more to less than 50%
D: less than 40%

<Solvent Resistance Test>

On a glass substrate, each of the compositions in each Examples and each Comparative Examples was coated by spin-coating to form a film having a thickness of 3.0 μm, and exposed to a light source at an expose amount of 240 mJ/cm² under nitrogen atmosphere without pressing the mold, and heated with an oven at 230° C. for 30 minutes, to thereby be cured. The cured film was dipped into a solvent mixture of 2-aminoethoxy-2-ethanol/N-methyl pyrrolidone (=1/1 volume ratio) at 70° C. for 15 minutes, and change between before and after the dip was evaluated as follows:

A: change of the film thickness was less than 1%
B: change of the film thickness was from 1% or more to less than 2%
C: change of the film thickness was from 2% or more to less than 4%
D: change of the film thickness was 4% or more.

<Evaluation of Transmission>

On a glass substrate, each of the compositions in each Examples and each Comparative Examples was coated by spin-coating to form a film having a thickness of 3.0 μm, and exposed to a light source at an expose amount of 240 mJ/cm² under nitrogen atmosphere without pressing the mold, and heated with an oven at 230° C. for 30 minutes, to thereby be cured. Transmittance at 400 nm of the cured film was measured with UV-2400PC manufactured by Shimadzu Corporation. Examples 1 to 8 all showed the transmittance of 97% or more, and were more excellent than the others. Comparative Examples 1 and 2 were less than 90%.

TABLE 4

| | Viscosity | Pattern Accuracy | Peelability | Surface Hardness | Elastic Recovery | Solvent Resistance |
|---|---|---|---|---|---|---|
| Example 1 | 7.2 | A | A | A | B | A |
| Example 2 | 7.5 | A | A | B | B | B |
| Example 3 | 8.5 | A | A | A | A | A |
| Example 4 | 15.5 | A | A | A | A | A |
| Example 5 | 10.5 | A | A | A | A | B |
| Example 6 | 12.5 | A | B | A | A | A |
| Example 7 | 8.5 | A | B | A | A | A |
| Example 8 | 7.0 | A | A | A | B | A |
| Example 9 | 20.0 | C | C | A | A | A |
| Comp. Exam. 1 | 5.6 | A | B | D | D | C |
| Comp. Exam. 2 | 8.0 | A | C | D | D | D |

As is clear from Table 4, the compositions in Examples 1 to 9, which comprise the (meth)acrylate represented by the formula (1) of the invention and the photopolymerization initiator were excellent in all of the pattern accuracy, the peelability, the surface hardness, the elastic recovery ratio and the solvent resistance of the cured products. On the other hand, the composition in Comparative Example 1, which comprises (meth)acrylate, ethylene glycol di(meth)acrylate and benzyl (meth)acrylate as a polymerizable unsaturated monomer instead of the (meth)acrylate represented by the formula (1) of the invention, was poor in the surface hardness, the elastic recovery ratio and the solvent resistance. The composition of Comparative Example 2, in which the benzoic acid aryl ester described in JP-A-H-10-251473 is used, was poor in the peelability, the surface hardness, the elastic recovery ratio and the solvent resistance of the cured products.

[Industrial Applicability]

The invention can provide a (meth)acrylate compound excellent in photocurability, a curable composition using the same, which is excellent in all of pattern accuracy, peelability, surface hardness, elastic recovery ratio and solvent resistance of the cured films, a curable composition for photonanoimprints and a cured product of those curable compositions, and a method for manufacturing the cured product, especially a composition favorable to a permanent film in plat flat panel displays. The invention can provide a curable composition excellent in property for a residual film, light transmittance, mechanical property such as scratching resistance, and solvent resistance when the cured film was used as a protection film or a permanent film such as a spacer.

The invention claimed is:

1. A (meth)acrylate compound represented by the following formula (1):

[Chemical 1]

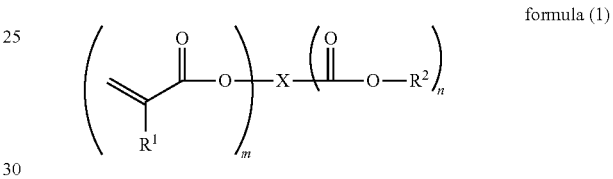

formula (1)

wherein R¹ represents a hydrogen atom or a methyl group, R² represents a linear or branched unsaturated hydrocarbon having carbon atoms of 2 to 6 and having a carbon-carbon double bond, X represents an organic group having carbon atoms of 1 to 10, m and n each are an integer of 1 to 3, and which satisfies the following (1) and/or (2):
(1) R¹ in the formula (1) is a hydrogen atom, X in the formula (1) is a benzene ring or a naphthalene ring, and m and n in the formula (1) each are 1 or 2;
(2) the (meth)acrylate compound has at least one partial structure selected from hydroxybenzoic acid, dihydroxybenzob acid, dihydroxyphthalic acid and dihydroxynaphthoic acid.

2. The (meth)acrylate compound according to claim 1, wherein R² in the formula (1) is —CH₂—CH=CH₂.

3. The (meth)acrylate compound according to claim 1, wherein R¹ in the formula (1) is a hydrogen atom.

4. The (meth)acrylate compound according to claim 1, which is selected from the following:

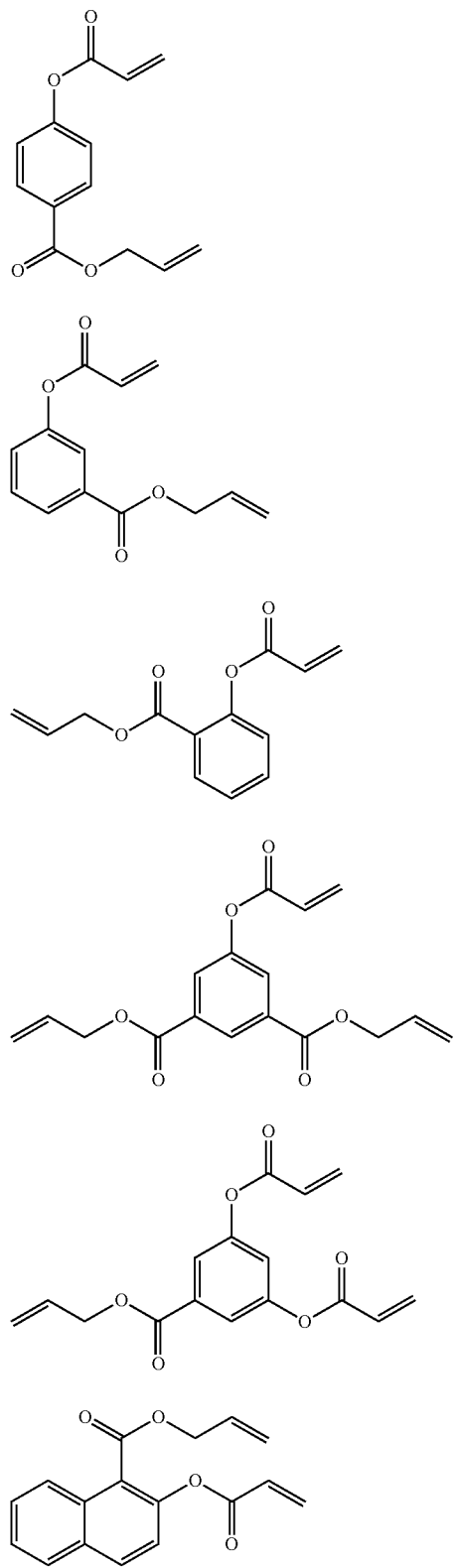
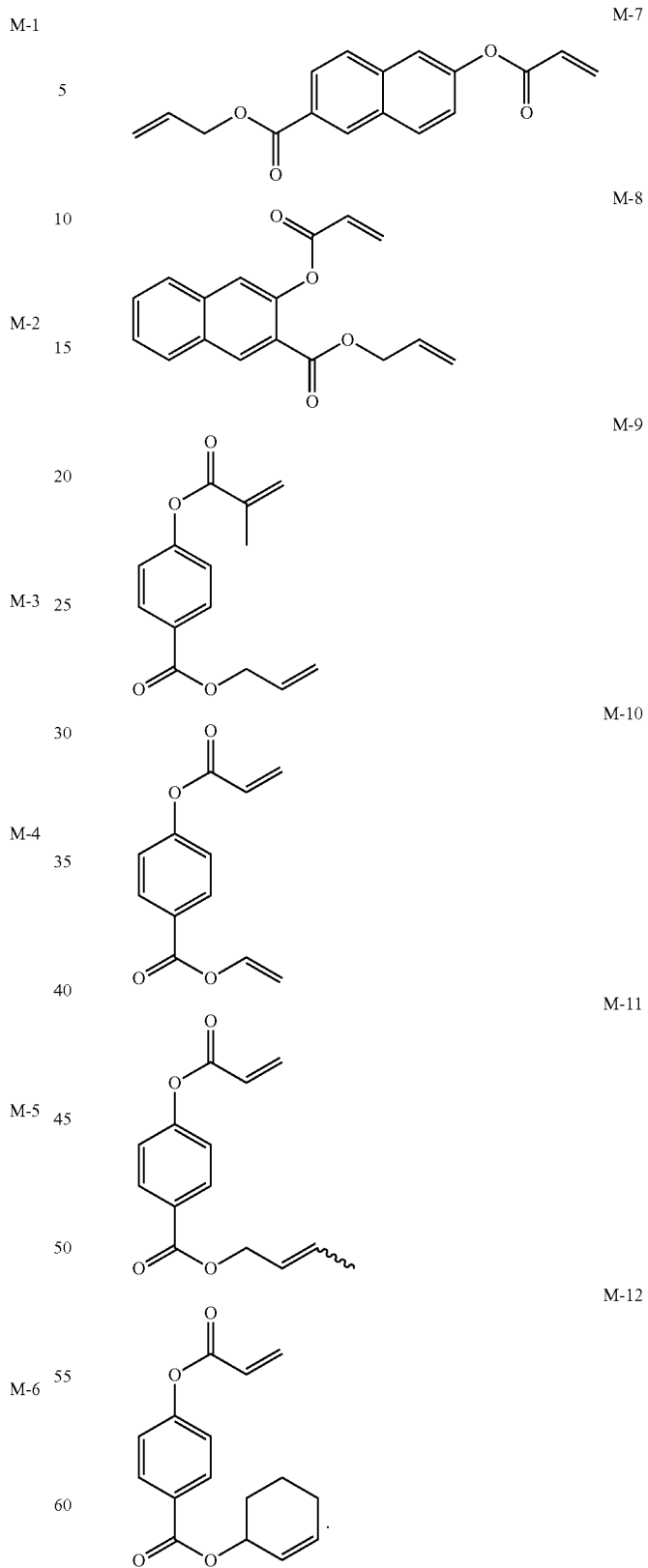
5. A curable composition comprising a photopolymerization initiator and a (meth)acrylate compound represented by the following formula:

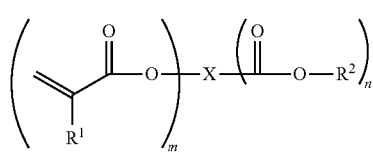

formula (1)

wherein $R^1$ represents a hydrogen atom or a methyl group, $R^2$ represents a linear or branched unsaturated hydrocarbon having carbon atoms of 2 to 6 and having a carbon-carbon double bond, X represents an organic group having carbon atoms of 1 to 10, m and n each are an integer of 1 to 3, and wherein the (meth)acrylate compound represented by the formula (1) satisfies the following (1) and/or (2):

(1) $R^1$ in the formula (1) is a hydrogen atom, X in the formula (1) is a benzene ring or a naphthalene ring, and m and n in the formula (1) each are 1 or 2;

(2) the (meth)acrylate compound has at least one partial structure selected from hydroxybenzoic acid, dihydroxybenzoic acid, dihydroxyphthalic acid and dihydroxynaphthoic acid.

6. The curable composition according to claim 5, wherein $R^2$ in the formula (1) is —$CH_2$—$CH$=$CH_2$.

7. The curable composition according to claim 5, wherein $R^1$ in the formula (1) is a hydrogen atom.

8. The curable composition according to claim 5, the (meth)acrylate compound is selected from the following:

M-1

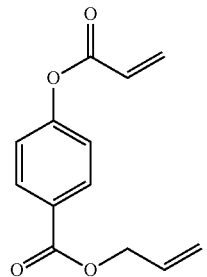

M-2

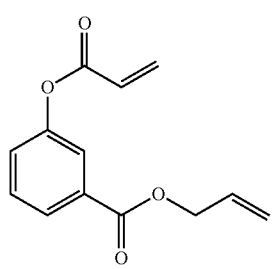

M-3

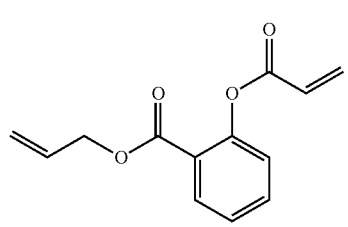

M-4

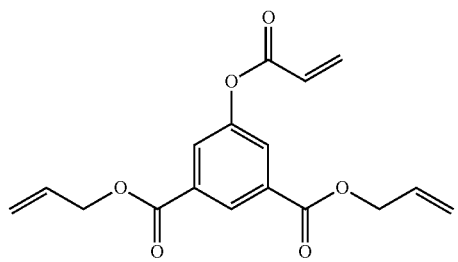

M-5

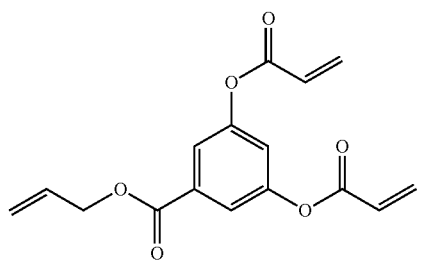

M-6

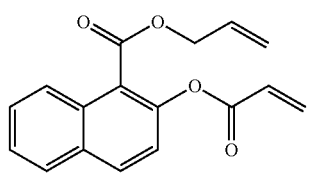

M-7

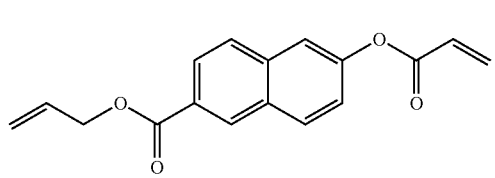

M-8

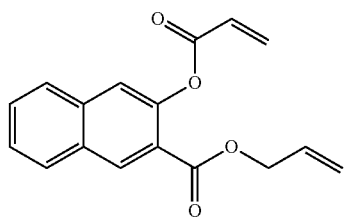

M-9

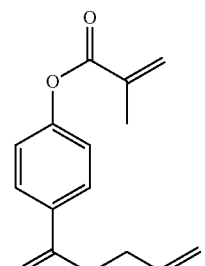

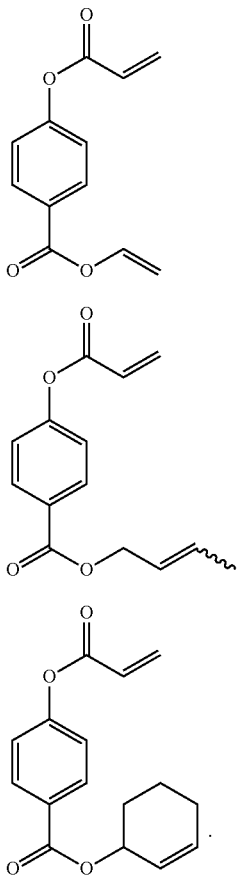

9. The curable composition according to claim 5, which further comprises a polymerizable monomer other than the (meth)acrylate compound represented by the formula (1).

10. The curable composition according to claim 9, wherein the polymerizable monomer other than the (meth)acrylate compound represented by the formula (1) is a (meth)acrylate having a cyclic structure.

11. The curable composition according to claim 5, which further comprises a surfactant and/or an antioxidant.

12. The curable composition according to claim 5, which has a viscosity of 3 to 18 mPa·s at 25° C.

13. The curable composition according to claim 5, which is curable with photoirradiation and/or heating.

14. A curable composition for nanoimprints, comprising a photopolymerization initiator and a (meth)acrylate compound represented by the following formula:

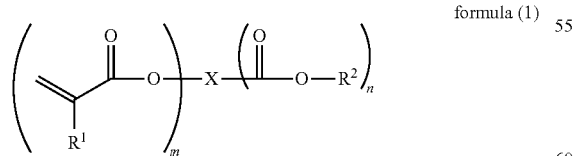

formula (1)

wherein $R^1$ represents a hydrogen atom or a methyl group, $R^2$ represents a linear or branched unsaturated hydrocarbon having carbon atoms of 2 to 6 and having a carbon-carbon double bond, X represents an organic group having carbon atoms of 1 to 10, m and n each are an integer of 1 to 3, and wherein the (meth)acrylate compound represented by the formula (1) satisfies any one of the following (3) to (6):

(3) $R^2$ in the formula (1) is —$CH_2$—$CH$=$CH_2$, (4) $R^1$ in the formula (1) is a hydrogen atom, (5) X in the formula (1) is a benzene ring or a naphthalene ring, (6) m and n in the formula (1) each are 1 or 2.

15. The curable composition for nanoimprints according to claim 14, wherein the (meth)acrylate compound represented by the formula (1) satisfies at least one of (5) and (6).

16. The curable composition for nanoimprints according to claim 14, wherein the (meth)acrylate compound represented by the formula (1) is selected from the following:

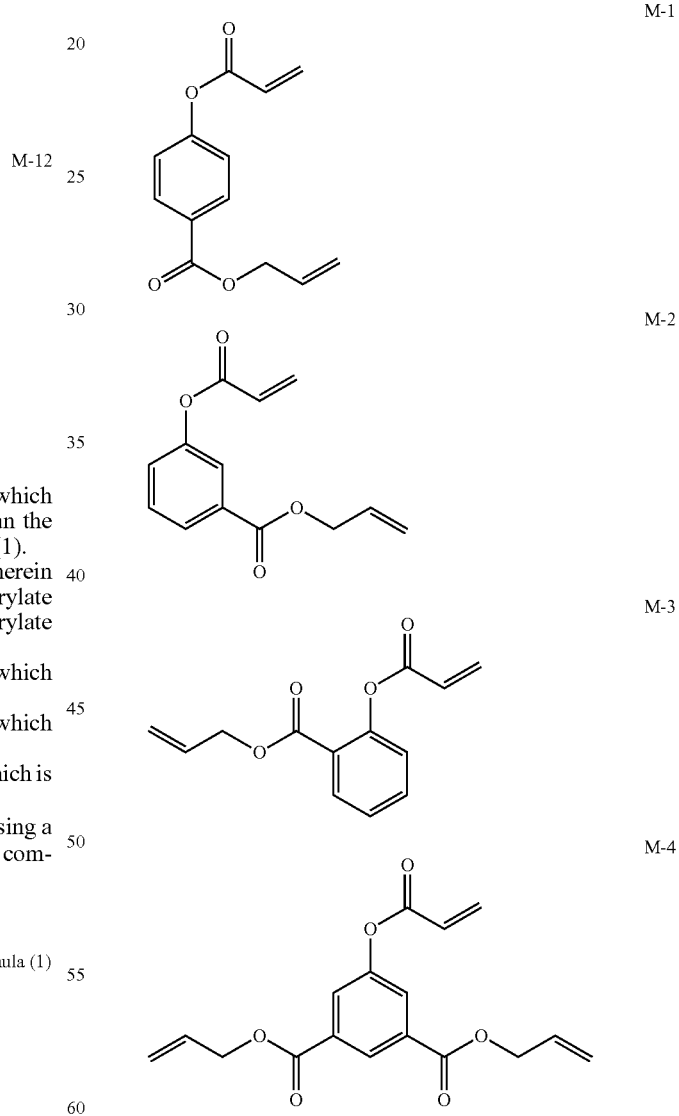

M-5
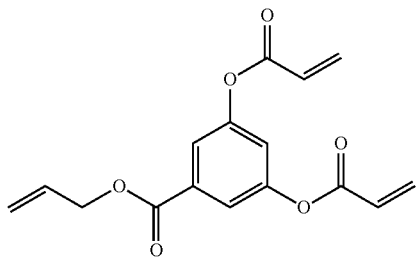

M-6
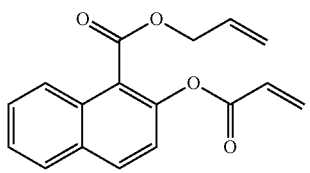

M-7
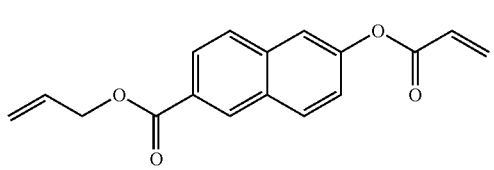

M-8
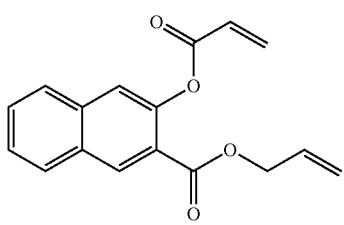

M-9
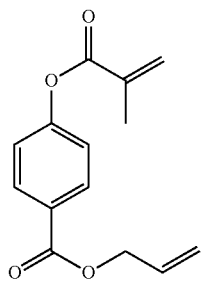

M-10
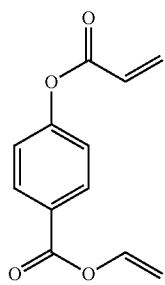

M-11
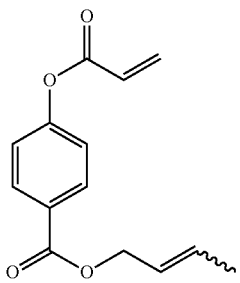

M-12
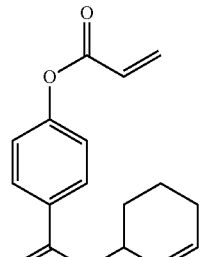
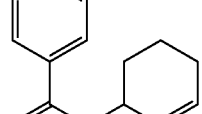

17. A cured product obtained by curing the curable composition according to claim 5.

18. A method for manufacturing a cured product, which comprises curing the curable composition according to claim 5.

19. A method for manufacturing a cured product, which comprises applying the curable composition according to claim 5 onto a substrate to form a patterning layer thereon, pressing a mold against a surface of the patterning layer, and irradiating the patterning layer with light.

20. The method for manufacturing a cured product according to claim 19, which further comprises heating the patterning layer irradiated with light.

* * * * *